United States Patent [19]
Prammer et al.

[11] Patent Number: 5,936,405
[45] Date of Patent: *Aug. 10, 1999

[54] SYSTEM AND METHOD FOR LITHOLOGY-INDEPENDENT GAS DETECTION USING MULTIFREQUENCY GRADIENT NMR LOGGING

[75] Inventors: Manfred G Prammer, West Chester, Pa.; Duncan Mardon, Kingwood; George R Coates, Austin, both of Tex.; Melvin N Miller, Wynnewood, Pa.

[73] Assignee: Numar Corporation, Malvern, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/719,316

[22] Filed: Sep. 25, 1996

Related U.S. Application Data

[60] Provisional application No. 60/004,241, Sep. 25, 1995.

[51] Int. Cl.$^6$ ............................................... G01R 33/44
[52] U.S. Cl. ................................ 324/303; 324/307
[58] Field of Search ............................ 324/300, 303, 324/307, 309, 318

[56] References Cited

U.S. PATENT DOCUMENTS

| | | | |
|---|---|---|---|
| 3,508,438 | 4/1970 | Alger et al. ................................ | 73/152 |
| 4,710,713 | 12/1987 | Taicher et al. ........................... | 324/303 |
| 4,717,876 | 1/1988 | Masi et al. ............................... | 324/303 |
| 4,717,877 | 1/1988 | Taicher et al. ........................... | 324/303 |
| 4,717,878 | 1/1988 | Taicher et al. ........................... | 324/303 |

(List continued on next page.)

FOREIGN PATENT DOCUMENTS

| | | | |
|---|---|---|---|
| 0 581 666 A3 | 2/1994 | European Pat. Off. ......... | G01V 3/32 |
| 0 649 035 B1 | 4/1995 | European Pat. Off. ......... | G01V 3/32 |

OTHER PUBLICATIONS

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Carr et al., "Effects of Diffusion on Free Precision in Nuclear Magnetic Resonance Experiments," *Physical Review*, vol. 94, No. 3 (May 1, 1954), pp. 630–638.

*Schlumberger Wireline & Testing*, "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

(List continued on next page.)

*Primary Examiner*—John Barlow
*Assistant Examiner*—Hien Vo
*Attorney, Agent, or Firm*—Pennie & Edmonds LLP

[57] ABSTRACT

A well logging system and method for detecting the presence and estimating the quantity of gaseous and liquid hydrocarbons in the near wellbore zone. The system uses a gradient-based, multiple-frequency NMR logging tool to extract signal components characteristic for each type of hydrocarbons. To this end, a new data acquisition method is proposed in which measurements at different frequencies are interleaved to obtain, in a single logging pass, multiple data streams corresponding to different recovery times and/or diffusivity for the same spot in the formation. The resultant data streams are processed to determine mineralogy-independent water and hydrocarbon saturations and porosity estimates. Gas and oil saturations are used to obtain accurate estimates of the water content, permeability and other parameters of interest.

29 Claims, 15 Drawing Sheets

U.S. PATENT DOCUMENTS

| | | | |
|---|---|---|---|
| 4,728,892 | 3/1988 | Vinegar et al. | 324/309 |
| 4,933,638 | 6/1990 | Kenyon et al. | 324/303 |
| 5,023,551 | 6/1991 | Kleinberg et al. | 324/303 |
| 5,212,447 | 5/1993 | Paltiel | 324/300 |
| 5,280,243 | 1/1994 | Miller | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,412,320 | 5/1995 | Coates | 324/303 |
| 5,432,446 | 7/1995 | Macinnis et al. | 324/303 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,596,274 | 1/1997 | Sezginer | 324/303 |
| 5,680,043 | 10/1997 | Hurlimann et al. | 324/303 |

OTHER PUBLICATIONS

Kleinberg et al., "Novel NMR Apparatus for Investigating an External Sample," *Journal of Magnetic Resonance*, (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservior Sandstrones," *Society of Petroleum Engineers* (1990), pp. 733–741.

Miller et al., "Spin Echo Magnetic Resonance Logging: Porosity and Free Fluid Index Determination," *Society of Petroleum Engineers* (1990), pp. 321–334.

Kenyon et al., "Pore–Size Distribution and NMR in Microporous Cherty Sanstones," SPWLA Thirtieth Annual Logging Symposium (Jun. 11–14, 1989), pp. 1–24.

*Schlumberger Technology News—Oilfeld Bulletin*, "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs," SPWLA 35th Annual Logging Symposium (Jun. 26–29, 1995).

Prammer, M.G., "NMR Pore Size Distributions and Permeability at the Well Site,", *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Jackson et al., "Western Gas Sands Project Los Alamos NMR Well Logging Tool Development," Los Alamos National Laboratory (Oct. 1981–Sep. 1982) pp. 1–28.

Clavier et al., "The Theoretical and Experimental Bases for the 'Dual Water' Model for the Interpretation of Shaly Sands," *Journal of Petroleum Technology* (Apr. 1984), pp. 3–15.

Waxman et al., "Electrical Conductivities in Oil–Bearing Shaly Sands," Society of Petroleum Engineers Journal (1968) pp. 107–122.

SYSTEM AND METHOD FOR LITHOLOGY-INDEPENDENT GAS DETECTION USING MULTIFREQUENCY GRADIENT NMR LOGGING

CROSS-REFERENCES TO RELATED APPLICATIONS

This application claims the benefit of U.S. Provisional Application No. 60/004,241 filed Sep. 25, 1995.

BACKGROUND OF THE INVENTION

The present invention relates to nuclear magnetic resonance (NMR) logging and is directed more specifically to a system and method for detecting the presence and estimating the quantity of gaseous and liquid hydrocarbons in the near wellbore zone.

Petrophysical parameters of a geologic formation which are typically used to determine whether the formation will produce viable amounts of hydrocarbons include the formation porosity PHI, fluid saturation S, the volume of the formation, and its permeability K. Formation porosity is the Dore volume per unit volume of formation; it is the fraction of the total volume of a sample that is occupied by pores or voids. The saturation S of a formation is the fraction of a its pore volume occupied by the fluid of interest. Thus, water saturation $S_W$ is the fraction of the pore volume which contains water. The water saturation of a formation can vary from 100% to a small value which cannot be displaced by oil, and is referred to as irreducible water saturation $S_{Wirr}$. For practical purposes it can be assumed that the oil or hydrocarbon saturation of the formation $S_O$ is equal to $S_O = 1 - S_W$. Obviously, if the formation's pore space is completely filled with water, that is if $S_W = 1$, such a formation is of no interest for the purposes of an oil search. On the other hand, if the formation is at $S_{Wirr}$ it will produce all hydrocarbons and no water. Finally, the permeability K of a formation is a measure of the ease with which fluids can flow through the formation, i.e., its producibility.

Nuclear magnetic resonance (NMR) logging is among the most important methods which have been developed to determine these and other parameters of interest for a geologic formation and clearly has the potential to become the measurement of choice for determining formation porosity. At least in part this is due to the fact that unlike nuclear porosity logs, the NMR measurement is environmentally safe and is unaffected by variations in matrix mineralogy. The NMR logging method is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the so called spin-spin relaxation time constant $T_2$ (also known as transverse relaxation time) which is an expression of the relaxation due to non-homogeneities in the local magnetic field over the sensing volume of the logging tool.

Another measurement parameter used in NMR well logging is the formation diffusion D. Generally, diffusion refers to the motion of atoms in a gaseous or liquid state due to their thermal energy. The diffusion parameter D is dependent on the pore sizes of the formation and offers much promise as a separate permeability indicator. In an uniform magnetic field, diffusion has little effect on the decay rate of the measured NMR echoes. In a gradient magnetic field, however, diffusion causes atoms to move from their original positions to new ones, which moves also cause these atoms to acquire a different phase shifts compared to atoms that did not move, and will thus contribute to a faster rate of relaxation. Therefore, in a gradient magnetic field diffusion is a logging parameter which can provide independent information about the structure of the geologic formation of interest, the properties of the fluids in it, and their interaction.

It has been observed that the mechanisms which determine the values of $T_1$, $T_2$ and D depend on the molecular dynamics of the sample being tested In bulk volume liquids, typically found in large pores of the formation, molecular dynamics is a function of molecular size and inter-molecular interactions which are different for each fluid. Thus, water, gas and different types of oil each have different $T_1$, $T_2$ and D values. On the other hand, molecular dynamics in a heterogeneous media, such as a porous solid which contains liquid in its pores, differs significantly from the dynamics of the bulk liquid and generally depends on the mechanism of interaction between the liquid and the pores of the solid media. It will thus be appreciated that a correct interpretation of the measurement parameters $T_1$, $T_2$ and D can provide valuable information relating to the types of fluids involved, the structure of the formation and other well logging parameters of interest.

A major barrier to using NMR logging alone for determination of porosity and other parameters of interest in the past has been the widespread belief that a near-wellbore NMR measurement cannot detect hydrocarbon gases. Failure to recognize such gases may result in their contribution being misinterpreted as bound fluid, which mistake may in turn result in excessively high irreducible water saturations and correspondingly incorrect permeability estimates. It has recently been found, however, that the NMR properties of gas are in fact quite different from those of water and oil under typical reservoir conditions and thus can be used to quantify the gas phase in a reservoir. More specifically, the Magnetic Resonance Imaging Log (MRIL®) tools of NUMAR Corporation have registered the gas effect as distortion in the bound volume irreducible (BVI) and/or free fluid index (FFI) measurements.

In a recent paper, entitles "NMR Logging of Natural Gas Reservoirs," paper N, presented at the 36th Annual SPWLA Symposium, Paris, Jun. 26–29, 1995, Akkurt, R. et al. have shown one approach of using the capabilities provided by NUMAR's MRIL® tool for detection of gas. The content of the Akkurt et al paper is incorporated herein for all purposes. In this paper, the authors point out that NMR signals from gas protons are detectable, and derive $T_1$ relaxation and diffusion properties of methane-dominated natural gas mixtures at typical reservoir conditions. The magnetic field gradient of the MRIL® is used to separate and to quantify water, oil and gas saturations based solely on NMR data.

The results in the Akkurt paper are based on the NUMAR MRIL-C tool, the output of which is used to obtain $T_2$ spectra. $T_2$ spectra are extracted from the raw CPMG echo trains by breaking the total NMR signal M(t) into N components, called bins, according to the formula:

$$M(t) = \sum_{i=1}^{N} a_i \exp(-t/T_2)$$

where $a_i$ is the porosity associated with the i-th bin. Each bin is characterized by a fixed center transverse relaxation time $T_{2i}$. The total NMR porosity is then determined as the sum of the porosities $a_i$ in all bins. The $T_2$ spectrum model is discussed in detail; for example, in Prammer, M. G., "NMR Pore Size Distributions and Permeability at the Well Site," paper SPE 28368, presented at the 69-th Annual Technical Conference and Exhibition, Society of Petroleum Engineers, New Orleans, Sep. 25–28, 1994, the content of which is expressly incorporated herein for all purposes.

On the basis of the $T_2$ spectra, two specific methods for gas measurements are proposed in the Akkurt paper and will be considered briefly next to provide relevant background information. The first method is entitled "differential spectrum method" (DSM). The DSM is based on the observation that often light oil and natural gas exhibit distinctly separated $T_2$ measurements in the presence of a magnetic field gradient, even though they may have overlapping $T_1$ measurement values. Also, it has been observed that brine and water have distinctly different $T_1$ measurements, even though their $D_0$ values may overlap. The DSM makes use of these observations and is illustrated in FIG. 1 in a specific example for a sandstone reservoir containing brine, light oil and gas. According to the Akkurt et al. paper, two separate logging passes are made with different wait times $TR_l$ and $TR_s$, such that the longer time $TR_l \geq T_{1g}$, and the shorter time satisfies the relationship $T_{1g} \geq TR_s \geq 3T_{1wmax}$.

Due to the large $T_1$ contrast between the brine and the hydrocarbons, the water signal disappears when the spectra of the two signals are subtracted, as shown in FIG. 1. Thus, the differential $T_2$ spectrum contains only hydrocarbon signals. It should be noted that the subtraction of the $T_2$ spectra also eliminates all bound water, making the DSM very useful in shaly sands.

The second method proposed in the Akkurt et al. paper is called "shifted spectrum method" (SSM). Conceptually the method is based on the observation that since the surface relaxation for gas is negligible, the apparent $T_2$ relaxation can be expressed as:

$$\frac{1}{T_2} = \frac{1}{T_{2B}}\left[1 + \frac{(\gamma G \tau)^2 D T_{2B}}{3}\right]$$

where G is the magnetic field gradient, D is the diffusion coefficient, $\tau$ is half the interecho time, $\gamma$ is the gyromagnetic ratio and $T_{2B}$ refers to the bulk relaxation. It is known in the art that for gas, which is a non-wetting phase, $T_1 = T_{1B} \approx T_{2B}$. Therefore, given that the product $D_0 T_1$ of a gas after substitution in the expression above is an order of magnitude larger than oil and two orders of magnitude larger than brine, it can be seen that the already large $DT_1$ contrast of gas can be enhanced even further by increasing the interecho time $2\tau$ in order to allow the separation of two fluids that overlap in $T_1$. The SSM is based on the above concept and is illustrated in FIGS. 2A–B.

Specifically, FIG. 2A shows synthetic $T_2$ decay curves in a gas bearing zone. The solid curve is for the short interecho time ($\approx 0.6$ msec) and the dashed curve corresponds to a longer interecho time of about 2.4 msec. FIG. 2B illustrates the $T_2$ spectra obtained from the inversion of the synthetic echo trains in FIG. 2A. The solid spectrum corresponds to the shorter interecho time, while the dashed spectrum line corresponds to the longer interecho time. In FIG. 2B the solid spectrum line corresponds to both brine and gas. The signal from gas is shifted out of the detectability range, so that the single spectrum peak is due to brine.

While the DSM and the SSM methods discussed in the Akkurt et al. paper and briefly summarized above provide a possible working approach to detection of gas using solely NMR data, the methods also have serious disadvantages which diminish their utility in practical applications. Specifically, due to the fact that two separate logging passes are required, the Akkurt methods show relatively poor depth matching properties on repeat runs. Furthermore, subtraction of signals from different logging passes is done in the $T_2$ spectrum domain which may result in losing valuable information in the transformation process, especially when the received signals have low signal-to-noise ratios (SNRs). In fact, for a typical logging pass, low hydrocarbon index (HI) of the gases in the formation, and relatively long $T_1$ times generally lead to low SNR of the received signals. After transformation into the $T_2$ spectrum domain even more information can be lost, thus reducing the accuracy of the desired parameter estimates. Finally, the Akkurt et al. paper does not indicate ways of solving additional problems such as accounting for low gas saturation in the sensitive volume, the presence of gases other than methane, and the temperature dependency of the filed gradient.

In summary, while some techniques have been developed in the prior art to extract information about the structure and the fluid composition of a geologic formation, so far no consistent NMR well logging method has been proposed to accurately and efficiently interpret these measurement parameters by accounting for the different effects of individual fluids. This lack may lead to inaccurate or misleading log data interpretation which in turn can cause costly errors in the oil exploration practice. Therefore, there is a need for a NMR system and method for providing consistent and accurate evaluation of geologic formations using a combination of substantially simultaneous log measurements to take into account the effects of different fluids.

SUMMARY OF THE INVENTION

Accordingly, it is an object of the present invention to provide a system and method for accurately interpreting borehole NMR measurements made with a gradient NMR logging tool.

It is another object of the present invention to provide a NMR system and method for the simultaneous detection of gas and oil in a formation of interest.

It is a further object of the present invention to provide a NMR system and method for estimating the relative quantities of gas and oil associated with a geologic formation on the basis of a set of predetermined parameters and of NMR logging measurements.

It is yet another object of the present invention to determine hydrocarbon corrected water saturations for use in intrinsic permeability determinations.

These and other objects are accomplished in accordance with a preferred embodiment of the present invention by a novel system and method for the interpretation of NMR measurements of $T_1$, D and effective $T_2$ parameters made with a NMR logging tool using gradient magnetic field. The system and method of the present invention are based on a novel multi-frequency, gradient based logging tool providing the capability of conducting substantially simultaneous NMR measurements in adjacent non-overlapping resonant volumes of the geologic formation of interest. In particular, by hopping the resonant frequency of the device and thus sensing non-overlapping volumes of the formation, in accordance with a preferred embodiment of the present invention the time between experiments is reduced substantially without compromising the $T_1$ relaxations or adopting imprecise $T_1/T_2$ empirical relationships.

In accordance with a preferred embodiment of the method of the present invention, using the multi-frequency capabilities of the NMR tool a new data acquisition method is developed suitable for the detection of gas on the basis of at least two sets of data points corresponding to a long ($T_{RL}$) and short ($T_{RS}$) recovery times, respectively. To this end, a novel interleaved pulse sequence is proposed in which at least two CPMG pulses associated with a first resonant frequency are followed by at least two CPMG pulses associated with a second resonant frequency. Due to the fact that each resonant frequency excites protons in a separate volume of the formation, pairs of complex data points can be collected at substantially the same depth mark such that the first data point corresponds to a short recovery time $T_{RS}$ while the second data point corresponds to a long recovery time $T_{RL}$.

In accordance with a preferred embodiment of the present invention, the sequence of data pairs is used next to form two complex time-domain signal vectors x and y corresponding to the long and the short recovery times, respectively. Following calibration, a difference and a sum signal vectors (x−y) and (x+y) are formed. The difference signal is phase corrected to obtain a real-time signal using phase information from the sum signal. Next, matched filters corresponding to a gas phase and an oil phase are computed, in real time, using information about reservoir temperature, pressure and other known probe and/or formation properties. The phase-corrected difference signal is then filtered using the matched filters to separate oil and gas signal components from the input NMR signals. The output signals from the matched filters are next used to obtain gas- and oil-porosity estimates and further to reconstruct the oil and gas components in the original measurement signals. The reconstructed components are subtracted from the sum signal ½(x+y) to provide only the brine component of the original signal. This brine component is finally subjected to $T_2$ inversion to obtain an estimate of the irreducible water saturation and water porosity. To further increase the separation between different hydrocarbon phases in the formation, diffusion-weighted measurements can also be used according to the SSM approach.

The system and method in accordance with the present invention have been shown to be very sensitive due to the fact that the gas and oil components of the original signal are determined from the original signals, prior to $T_2$ spectrum inversion. The method of the present invention has been demonstrated to give more accurate parameter estimates than other presently available NMR logging techniques and can be used advantageously in low-porosity formations, where low signal-to-noise ratios (SNRs) tend to broaden all $T_2$ components. Additionally, corrections for hydrogen index (HI) and incomplete longitudinal recovery are also provided to calculate estimates of gas-filled porosity and to correct both apparent NMR porosity (MPHI) and free fluid index FFI, which are necessary to obtain accurate estimates of formation permeability.

BRIEF DESCRIPTION OF THE DRAWINGS

The invention will be described next in detail by reference to the following drawings in which.

DETAILED DESCRIPTION OF THE INVENTION

During the course of the description like numbers will be used to identify like elements shown in the figures. Bold face letters represent vectors, while vector elements and scalar coefficients are shown in standard print.

Equipment

In order to separate signal contributions from different fluids, an NMR tool must be able to operate in a three-dimensional parameter space: $T_2$ (transverse decay time) measured by a CPMG pulse-echo sequence: $T_1$ (longitudinal polarization time) measured by variable saturation-recovery times; and D (apparent, restricted diffusivity), measured by varying the CPMG pulse-echo spacing $\tau$ in the presence of a magnetic field gradient.

Figure 1:
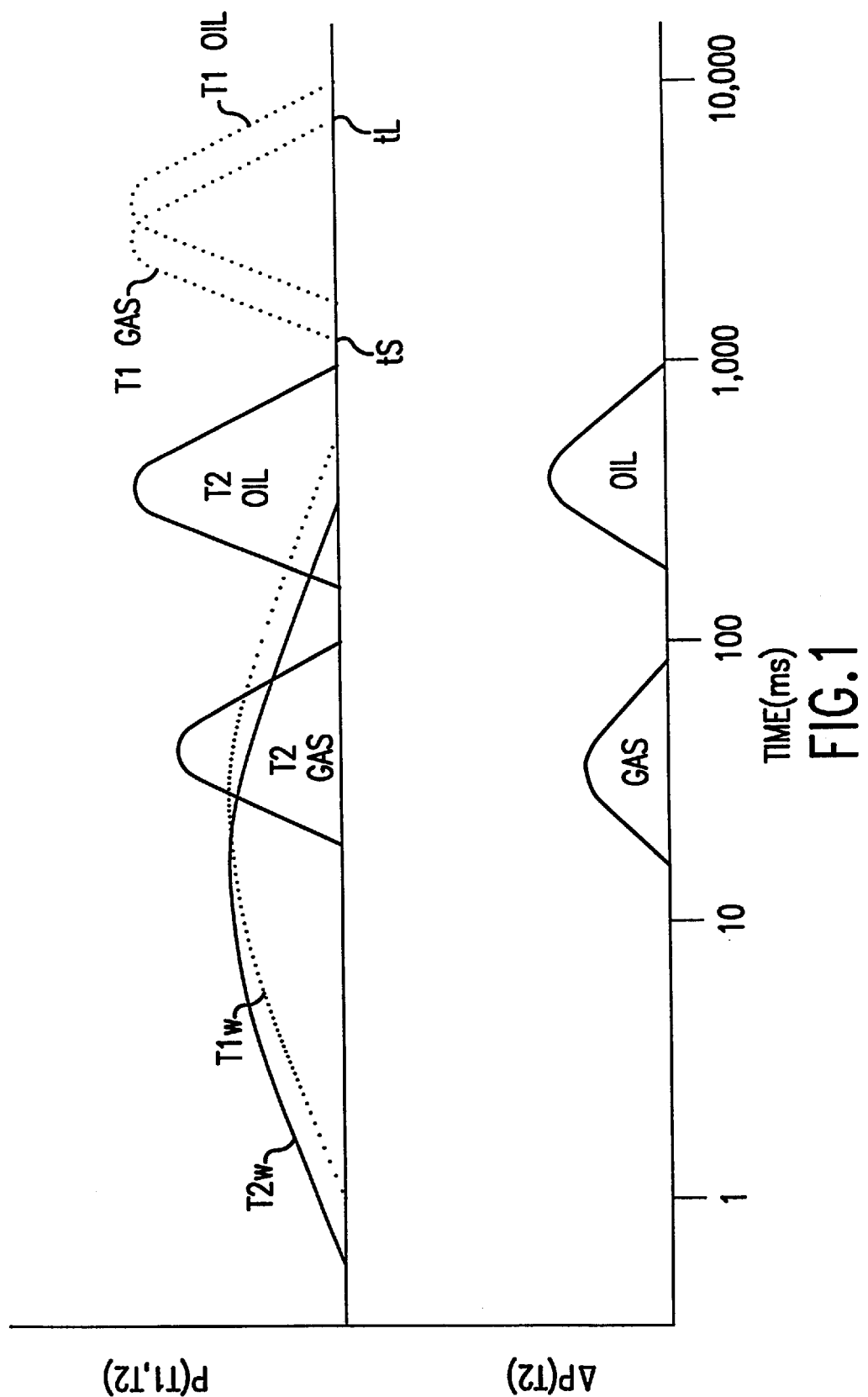
FIG. 1 is an illustration of the differential spectrum method for identifying the presence of gaseous components.
Figure 2A:
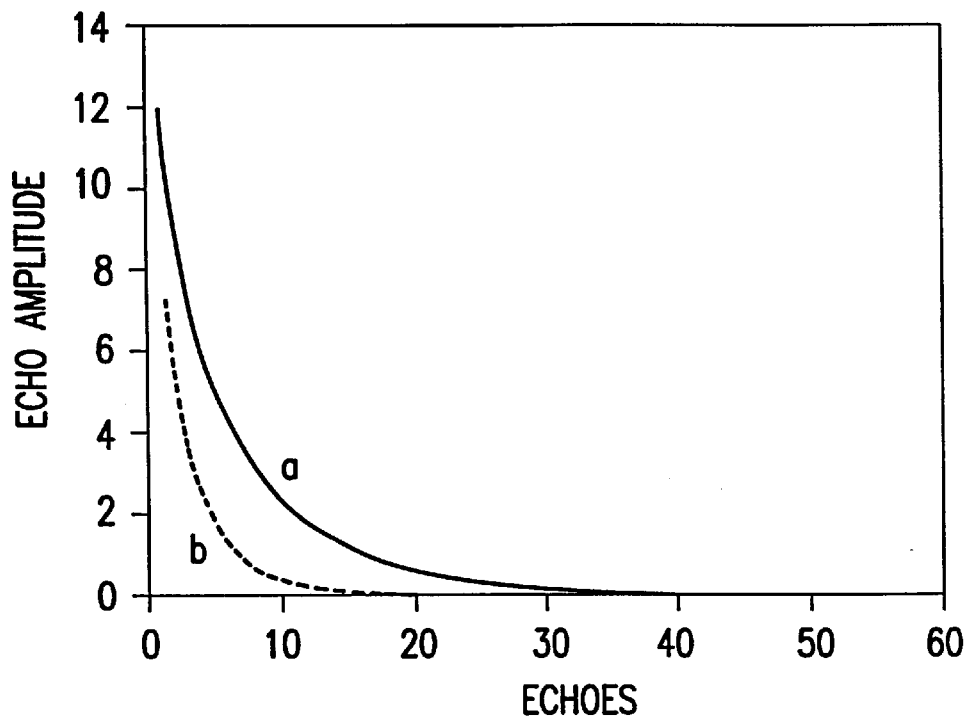
FIG. 2A illustrates synthetic $T_2$ decay curves used in the Shifted Spectrum method.
Figure 2B:
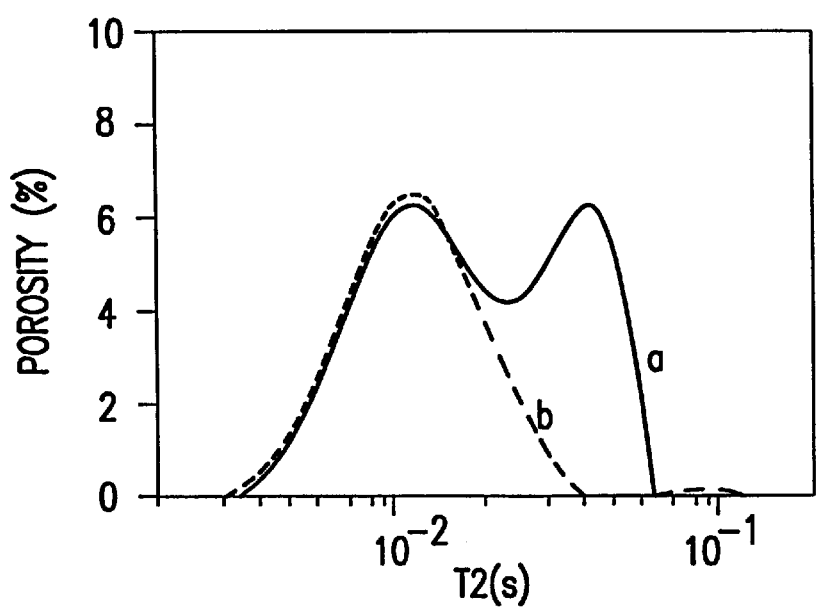
FIG. 2B shows $T_2$ spectra obtained from inversion of the synthetic echo trains in FIG. 2A.
Figure 3A:
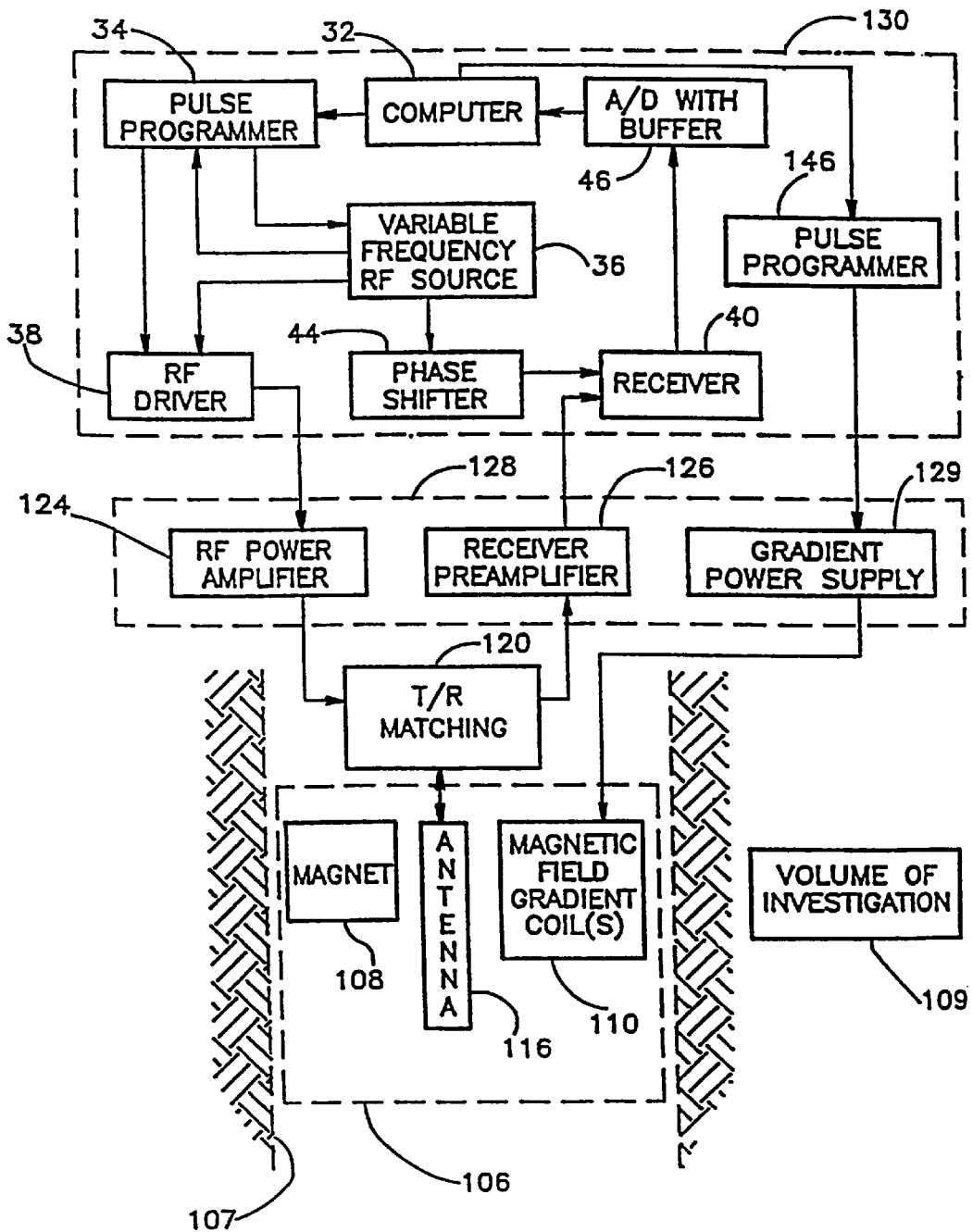
FIG. 3A shows a specific embodiment of the gradient-based logging tool of the present invention.

In a preferred embodiment of the present invention these measurements in a moving logging tool are enabled using the system illustrated schematically in FIGS. 3 (A–C). In particular, FIG. 3A illustrates, in relatively general form, apparatus for carrying out NMR borehole diffusion coefficient determinations in accordance with a preferred embodiment of the present invention. The apparatus includes a first portion 106, which is arranged to be lowered into a borehole 107 in order to examine the nature of materials in the vicinity of the borehole.

The first portion 106 comprises a magnet or a plurality of magnets 108 which generate a substantially uniform static magnetic field in a volume of investigation 109. The first portion 106 also comprises an RF antenna coil 116 which produces an RF magnetic field at the volume of investigation 109 which field is substantially perpendicular to the static magnetic field.

In addition to the static magnetic field gradient generated by magnet(s) 108, an optional magnetic field gradient coil, or plurality of coils, 110 can also be used to generate a magnetic field gradient at the volume of investigation 109. This additional contribution to the magnetic field has a field direction preferably collinear with the substantially uniform field and has a substantially uniform magnetic field gradient, which may or may not be switched on and off by switching the dc current flowing through the coil or coils 110. The magnet or magnets 108, antenna 116 and the gradient coil 110 constituting portion 106 are also referred to as a probe.

The antenna together with a transmitter/receiver (T/R) matching circuit 120 typically include a resonance capacitor, a T/R switch and both transmitter and to-receiver matching circuitry and are coupled to an RF power amplifier 124 and a receiver preamplifier 126. A power supply 129 provides the dc current required for the magnetic field gradient generating coils 110. All the elements described above are normally contained in a housing 128 which is passed through the borehole. Alternatively, some of the above elements may be located above ground.

Indicated as block 130 is control circuitry for the logging apparatus including a computer 32, which provides a control output to a pulse programmer 34 which receives an RF input from a variable frequency RF source 36. Pulse programmer 34 controls the operation of the variable frequency RF source 36 as well as an RF driver 38, which receives an input from variable frequency RF source 36 and outputs to RF power amplifier 124.

The complex time-domain signal from the RF receiver preamplifier 126 is supplied to an RF receiver 40 which optionally receives input from a phase shifter 44. Phase shifter 44 receives an input from variable frequency RF source 36. As discussed in more detail next, in a preferred embodiment of the present invention phase correction is done using signal processing algorithms instead. Receiver 40 outputs via an A/D converter with a buffer 46 to computer 32 for providing desired well logging output data for further use and analysis. Pulse programmer 34 controls the gradient coil power supply 129 enabling and disabling the flow of current, and hence the generation of static or pulsed field gradients, according to the commands of the computer 32. Some or all of the elements described hereinabove as being disposed in an above-ground housing, may instead be disposed below ground. Improved devices and measurement methods which can be used for the probe 106 are described generally in U.S. Pat. Nos. 4,710,713; 4,717,876; 4,717,877; 4,717,878, 5,212,447; 5,280,243; 5,309,098 and 5,412,320 all of which are commonly owned by the assignee of the present invention. A specific embodiment of the tool which can be used in accordance with the present invention is also discussed in detail in Chandler et al., "Improved Log Quality with a Dual-Frequency Pulsed NMR Tool," paper SPE 28365, presented at the 69-th Annual Technical Conference and Exhibition, Society of Petroleum Engineers, New Orleans, Sep. 25–28, 1994. The contents of these patents and the Chandler et al. paper are hereby expressly incorporated for all purposes.

Figure 3B:
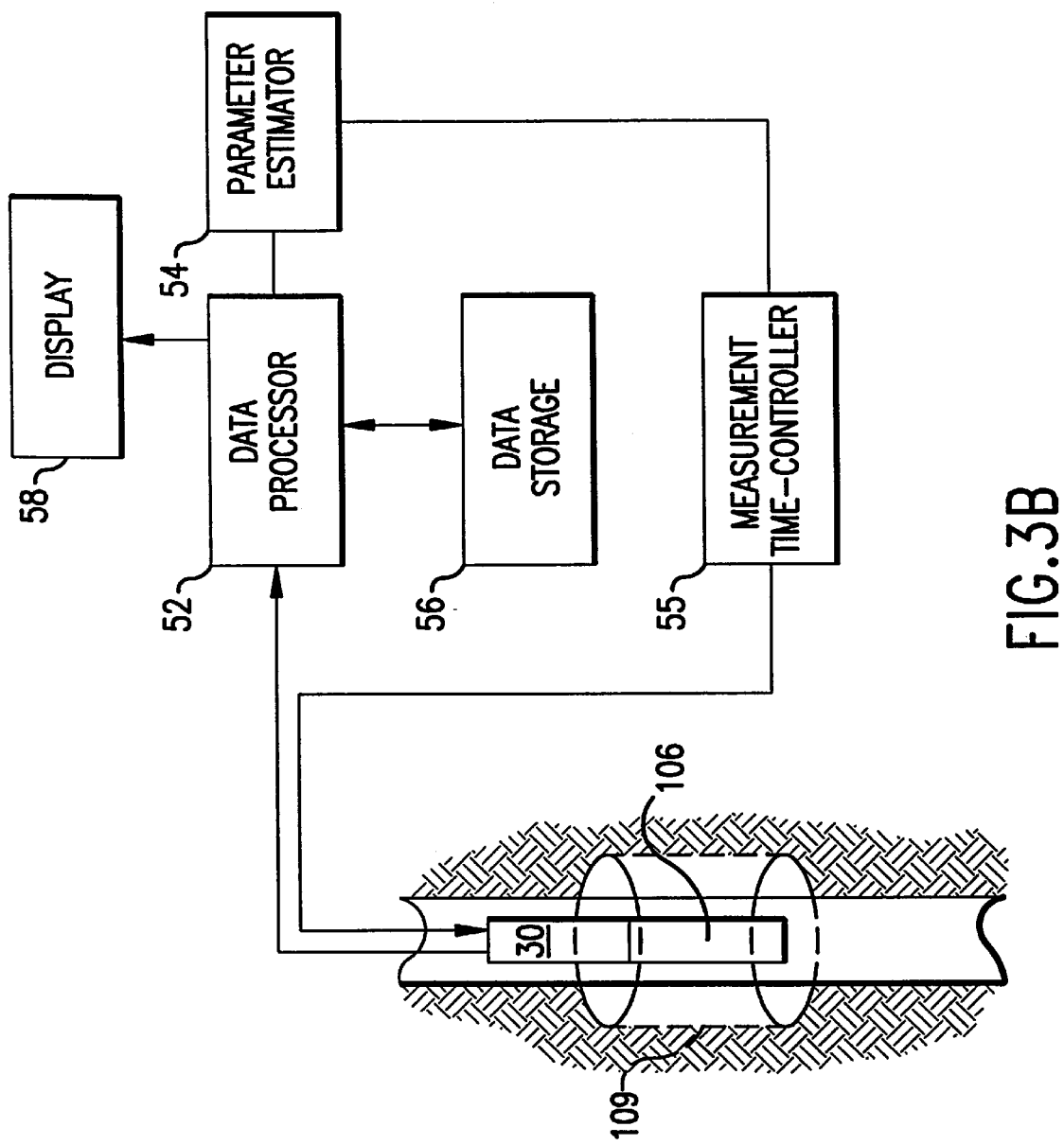
FIG. 3B is a block diagram of the system in accordance with a specific embodiment of the present invention which shows individual block components for controlling data collection, processing the collected data and displaying the measurement results.

FIG. 3B is a block diagram of the system in accordance with a specific embodiment of the present invention which shows individual block components for controlling data collection, processing of the collected data and displaying the measurement results. In FIG. 3B the MRI electronics 30 comprises an MRI probe controller and pulse echo detection electronics. The output signal from the detection electronics is processed by data processor 52 to analyze the relaxation characteristics of the sample. The output of the data processor 52 which in accordance with a preferred embodiment of the present invention comprises at least two complex time-domain data sets is provided to the parameter estimator 54. Measurement cycle controller 55 provides an appropriate control signal to the MRI probe. The processed data from the log measurement is stored in data storage 56. Data processor 52 is connected to display 58 which is capable of providing a graphical display of one or more measurement parameters, preferably superimposed on display data from data storage 56. The components of the system of the present invention shown in FIG. 3B can be implemented in hardware or software, or any combination thereof suitable for practical purposes.

As indicated above, the MRIL tool used in a preferred embodiment of the present invention is digitally based, so that raw echo data is digitized at the carrier frequency and all subsequent filtering and detection is performed in the digital domain. For the purposes of the present invention, the critical feature of the tool is its ability to operate at different frequencies.

Figure 3C:
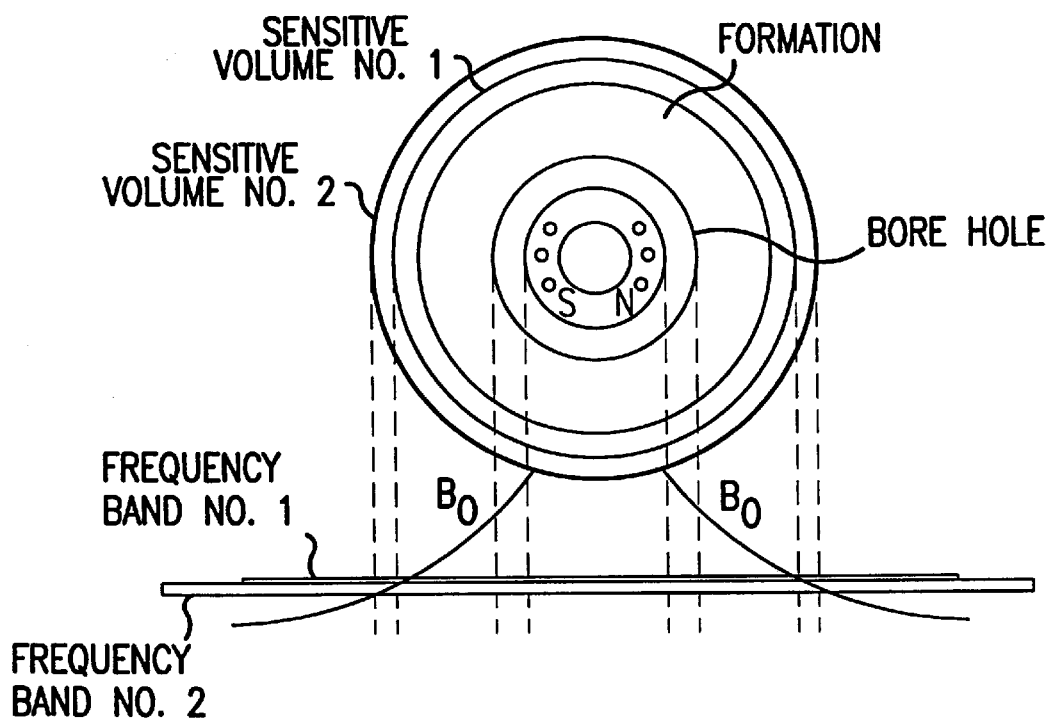
FIG. 3C illustrates the operation of a gradient logging tool in a multi-frequency mode at the example of dual-volume investigation.

Specifically, in a preferred embodiment the system of the present is capable of "hopping" from one operating frequency to another, the effect of which is to shift the radial position of the resonant volume for the tool. The frequency shift is selected in such manner that at least two non-overlapping resonant volumes are formed; each new resonant volume associated with a different frequency being filled with fully relaxed protons. Hopping between two or more (i.e., K) frequencies thus allows reducing the time between experiments approximately by a factor of K, without compromising complete $T_1$ measurements or adopting imprecise empirical $T_1/T_2$ relationships; the logging speed for the tool can accordingly be increased approximately K times. This feature is illustrated in FIG. 3C in which hopping between two different frequencies is shown to result in conducting measurements in two non-overlapping resonant volumes. In the specific example illustrated in FIG. 3C each frequency band is about 6 kHz wide and the two mean band frequencies are offset by about 15 kHz. This mode of operation forms two concentric annuli, each 0.04 inch (0.1 cm) thick, separated center to center by about 0.09 inches (0.23 cm).

The logging speed of the device used in a preferred embodiment of the present invention depends upon different factors including the SNR of the received signal, the desired log precision and vertical resolution, and the cycle time permitted by the $T_1$ parameter of the formation. Preferably, for greater than 95% recovery within a single resonant volume, the recovery time should satisfy the requirement $T_R \geq 3T_1$. As a consequence of the multi-frequency operation, the cycle time is only slightly longer than the $T_R$ normalized to the number of frequencies employed. (i.e. $T_C \approx T_R/2$ for two operating frequencies).

Figure 4:
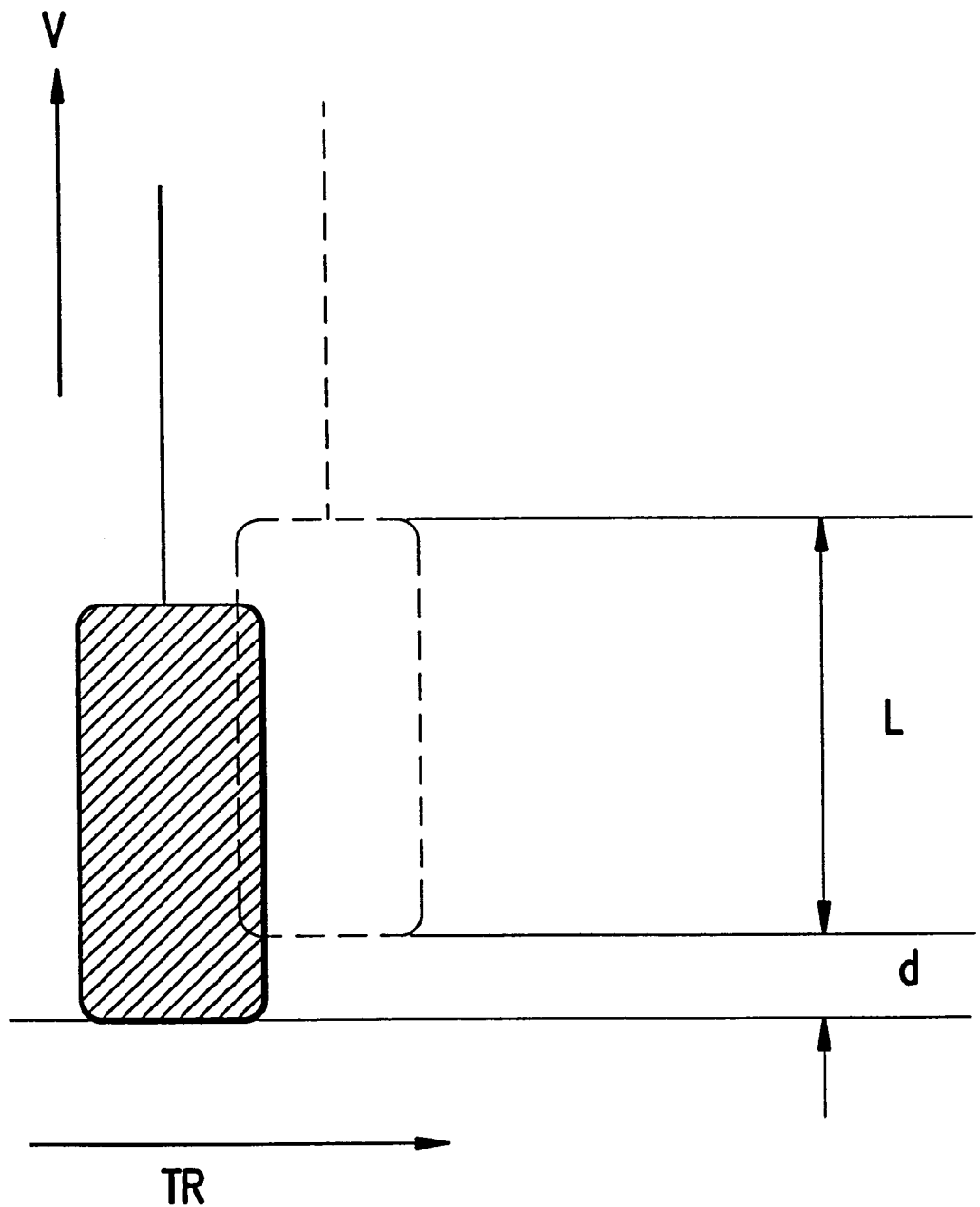
FIG. 4 is a schematic illustration of the connection between saturation-recovery time interval TR, logging speed v and aperture length L.

The MRIL tool used in a preferred embodiment of the present invention generally has a vertical excitation/response function that can be represented by a near-perfect rectangular aperture. In a specific embodiment, a high vertical resolution, 24" (60.96 cm) long aperture, or a lower vertical resolution, 43" (109.22 cm) long, aperture are used. In order to perform $T_1$-weighted signal measurements, as discussed in detail below, it is required that the formation volume being sensed remains substantially unchanged over the course of a recovery period. Specifically, for a moving tool, it has been determined that volume changes of about 10–20% still provide adequate measurement accuracy. This condition is illustrated in FIG. 4 which shows the relationships between saturation-recovery time interval $T_R$, logging speed v and aperture length L. Using the notations in FIG. 4, it is possible to impose either a minimum aperture length or a maximum tool logging speed requirement which must satisfy the condition for substantial measurement stationarity. For example, in the specific embodiment of a 24" long aperture, assuming recovery time $T_R$=2 s, and imposing a 10% accuracy requirement, it can be seen that the maximum allowed tool speed is v=5*2.4"/2s=6 ft/min (3.05 cm/sec). For the alternate configuration using a 43" long antenna, under the same assumptions the maximum tool speed is about 11 ft/min (5.588 cm/sec).

In accordance with the present invention, for the purposes of making $T_1$ weighted measurements with a moving logging tool at least one long saturation-recovery (SR) interval is required, preferably of about 8–10 sec. It should be noted that for such an interval logging data is substantially insensitive to vertical tool displacement because at the end of the interval the formation magnetization is already close to an equilibrium. The transverse magnetization left after a CPMG sequence is quickly dephased in the strong gradient field. At this point, a saturation-recovery (SR) measurement can be started, as known in the art. The recovered magnetization is read out by the next CPMG train.

In addition to the relatively long SR interval, one or more measurements are made in accordance with a preferred embodiment of the present invention using shorter recovery intervals, as described in more detail next.

Random lateral tool motion is a source of concern for the validity of the downhole $T_1$-weighted measurements in accordance with the present invention. The reason is that since the sensitive volume for the tool resembles a cylindrical slice of about 1–2 mm thickness, lateral swaying of the tool could cause an influx of fully polarized magnetization and thus give incorrect measurements. Studies of actual log data repeatedly acquired over the same zones, however, show monotonic recovery behavior of sequences with increasing SR intervals, indicating that lateral tool motion generally has a negligible effect on the actual measurements. Further evidence that side effects due to lateral motion of the tool are insignificant is provided by the consistency of MPHI and FFI measurements made with the tool, which are both independent of the $T_1$ parameter.

Another source of concern in NMR logging is the relatively shallow depth-of-investigation which, due to the generally cylindrical shape of the resonance volume of the tool, also depends on the borehole size. Thus, in some cases shallow depth-of-investigation along with the fact that invading fluid in the borehole replaces gas can lead to a reduction in the gas effect which can be sensed by the tool. It should be noted, however, that the MRIL tool's sensitive volume has an approximately 4" (10.16 cm) blind zone extending from the borehole wall. The presence of such blind zone effectively limits the influence of fluid invasion. Experimentally, in most cases residual hydrocarbon saturations seen by the tool have been shown to be sufficient for hydrocarbon detection purposes and can be close to uninvaded saturations.

The CPMG pulse sequences used with the MRIL tool in accordance with the present invention have been described generally in U.S. Pat. No. 5,212,447 assigned to the assignee of the present application. Also discussed in this patent are specific methods of conducting NMR measurements, including derivations of the diffusion coefficient D and/or $T_2$. The relevant portions of the disclosure of the U.S. Pat. No. 5,212,447 patent are expressly incorporated herein for all purposes. The MRIL tool used in accordance with a preferred embodiment of the present invention stores multiple pulse sequences downhole, in a memory (not shown in FIGS. 3A and B) within probe 106. These sequences are then activated by commands from the measurement time controller 55 of the surface system. At the surface, raw tool data are separated into data streams and associated with the correct calibration and correction tables in data processor 52. An essentially unlimited number of pulse sequences can be used quasi-simultaneously, as described in more detail next. In an alternative preferred embodiment of the present invention the operation of the tool can be re-programmed on command from surface controller 55.

Signal Modeling And Corrections

In accordance with a preferred embodiment of the present invention several parameters which correspond to the gas and the oil phases of the formation are computed in real time. Due to the fact that logging conditions dynamically change during the course of a pass, correction for various factors which may affect the accuracy of the measurements have to be made. In the following paragraphs, a brief discussion is presented on the specifics of the parameter computations and the required corrections used in accordance with a preferred embodiment of the present invention to estimate the relative quantities of gas and oil in a formation of interest.

1) Corrections for the influence of $T_1$ on diffusion measurements.

It is known in the art that the static field gradient required for downhole diffusion measurements induces stimulated echo effects within a CPMG echo train. These stimulated echoes partially undergo $T_1$ relaxation and therefore benefit less from the re-focusing effects of repeated $\pi$ pulses in a standard CPMG sequence. In accordance with a preferred embodiment of the present invention this problem can be treated by introducing the concept of "effective" relaxation times, as described in more detail next.

In particular, it is known that the classic Carr-Purcell expression for spin echo attenuation due to transverse relaxation and diffusion in a field gradient which, using the standard notations above, is given by the expression:

$$M_{xy}(t) = M_0 \exp\left(\left(-\frac{t}{T_2}\right) + \left(\frac{1}{3}\gamma^2 G^2 \tau^2 Dt\right)\right) \quad (1)$$

strictly speaking is valid only if: (a) the gradient G is small, or (b) if only the on-resonance portion of the spin spectrum is utilized. As indicated above, however, the MRIL tool operates with a relatively strong gradient field, on the order of about 15–25 G/cm. In addition, low signal-to-noise considerations make it necessary to utilize the full bandwidth of the tool, so that strong off-resonance effects are necessarily included in the echo signals. Thus, for example, even for the simplest $T_2/D$ experiment which requires at least two different pulse-echo spacings $\tau$ a correction in the expression in Eq. (1) is required in order to avoid systematic errors. Consequently, the observed echo decay signal has to be modeled as a complex superposition of longitudinal relaxation, transverse relaxation and different diffusion times.

Therefore, in accordance with the present invention, the signal observed at the N-th echo is modeled as a superposition of all possible combinations of transitions between transverse and longitudinal magnetization and is given by the expression:

$$M_{xy}(2\tau N) = M_0 \sum_{i=1}^{N} A_i \exp\left(-\frac{2\tau}{T_1}(N-i) - \frac{2\tau}{T_2}i - 2\left(N - \frac{2i}{3}\right)\gamma^2 G^2 \tau^3 D\right) \quad (2)$$

Using the expression in Eq. (2), the effect of diffusion dephasing is taken into account by introducing "effective" transverse relaxation times $T_1^{\dagger}$ and $T_2^{\dagger}$ given by the following expressions:

$$1T_1^{\dagger} = 1/T_1 = \gamma^5 G^2 \tau^2 D$$
$$1T_2^{\dagger} = 1/T_2 1/3 \cdot \gamma^2 G^2 \tau^2 D \quad (3)$$

It can be shown that direct echoes (i=N) decay with a rate $1/T_2^{\dagger}$; indirect echo decay (i<N) is controlled by $1/T_1^{\dagger}$ and by $1/T_2^{\dagger}$. Without diffusion, indirect echoes decay either slower or at the same rate as direct echoes. With very fast diffusion, however, indirect echoes drop out faster than direct ones The effect on combined echo amplitudes primarily depends on the receiver's bandwidth and has been determined to require an about 15% correction at high diffusion rates.

It should be noted that the expressions for the effective relaxation rates in Eq. (3) refer to the echo decay process, and not to the recovery of longitudinal magnetization, which is controlled by $T_1$. For gases, both effective relaxation times are dominated by the diffusion term in a gradient field and therefore $T_1 \gg T_1^{\dagger} \approx T_2^{\dagger}/3$. In this case, the echo train decays slightly faster than expected, and an analysis based on the standard Carr-Purcell formula will overestimate the diffusion parameter D. This problem is corrected by inserting into the Carr-Purcell formula of an effective pulse-echo spacing $\tau_{eff}$, which incorporates the influence of both pulse width and receiver bandwidth:

$$1/T_2^{\dagger} = 1/3 \cdot (\tau_{eff} \gamma G)^2 D \quad (4)$$

It has been determined that for the MRIL systems used in accordance with a preferred embodiment of the present invention, the ratio $\tau_{eff}/\tau = 1.08$, thus resulting in a 16% correction for calculated gas diffusivities.

2) Magnetic field gradient and probe temperature.

As evident from Eq. (4), the prediction of $T_2^{\dagger}$ in the gas phase generally requires knowledge of the field gradient G, which is dependent on the probe temperature. A specific example of measurements of the depth-of-investigation (diameter of the sensitive zone) and the magnetic field gradient values, as functions of probe temperature, are summarized in Table 1.

TABLE 1

Sensitive diameter and magnetic field gradient of an MRIL ®/C 6" tool as functions of probe temperature

| Temperature | Diameter | Field Gradient |
|---|---|---|
| 25° C. | 40.6 cm | 16.6 G/cm |
| 50° C. | 39.7 cm | 17.0 C/cm |
| 75° C. | 38.9 cm | 17.4 G/cm |
| 100° C. | 37.8 cm | 17.9 G/cm |
| 125° C. | 36.8 cm | 18.4 G/cm |
| 150° C. | 35.8 cm | 18.9 G/cm |

Typical values used in Eq. (4) are $\tau_{eff} = 0.65$ ms, $\gamma = 26750 s^{-1} G^{-1}$, and G=18 G/cm. Probe temperature, as reported by a sensor embedded in the permanent magnet of the MRIL tool, is always recorded, which allows the calculation of the field gradient G at any point on the log.

3) Parameterization of HI, $T_1$ and $T_2$

The matched filter signal processing method of the present invention, described in more detail below, requires the calculation of hydrocarbon (oil and gas) signatures. These components are assumed to be the non-wetting phase, i.e., to be generally characterized by their bulk relaxation properties. As known in the art, the effects of temperature and pressure on $T_1$ and D of the gas phase substantially cancel each other, resulting in fairly stable and predictable values for both parameters, for which mathematical expressions are available. On the other hand, the corresponding values for the oil phase are generally dependent on the formation and are determined in accordance with the present invention from sample measurements conducted prior to the logging experiment.

Figure 5A:
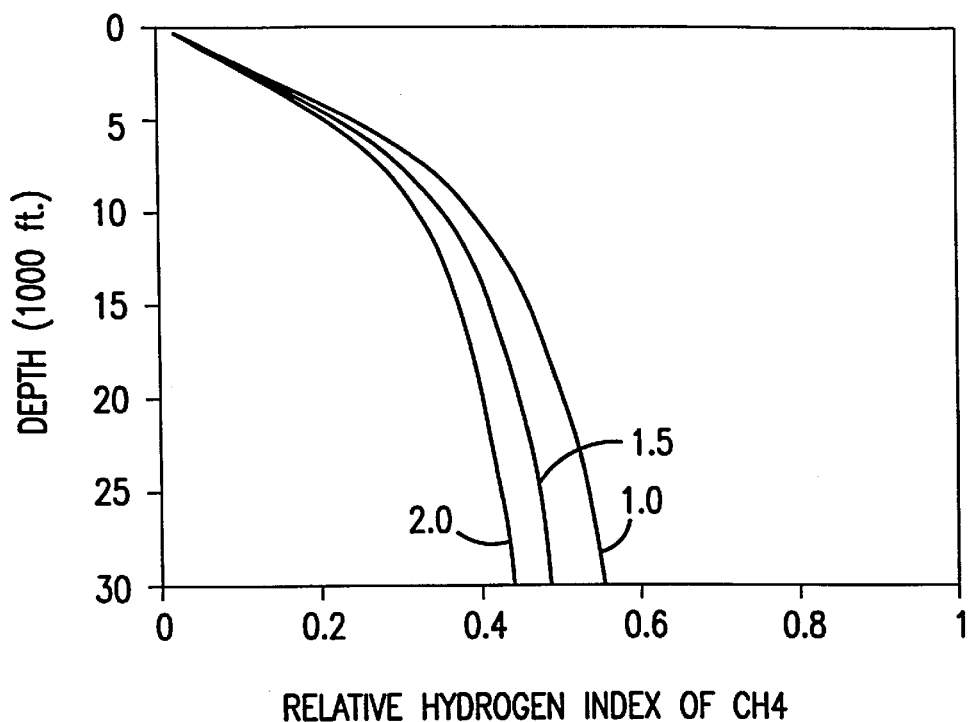
FIG. 5A shows the hydrogen index (HI) of methane as a function of depth at temperature gradients of 1, 1.5 and 2° F./100 ft.

In particular, the hydrogen index (HI) of oil is assumed to be 1.0. The measured drop in NMR porosity is typically observed in gas zones, because $HI_g < 1$. Most natural gases are predominantly methane. FIG. 5A shows $HI_g$ variations between about 0.2 and 06 for a methane gas under typical conditions. In overpressured reservoirs $HI_g$ can be about 0.7. Accordingly, the gas HI is sufficient to give readily detectable signals from gas. For methane gas, in accordance with a preferred embodiment of the present invention the corresponding index $HI_g$ is estimated mathematically using the expression $2.25 \times \rho$, where $\rho$ is the gas density in g/cm$^3$, calculated by solving the equation of state. For gases other than methanes or for mixed gases, the multiplying factor is less than 2.25. For example, for a typical gas mix, characterized as $C_{1.1}H_{4.2}$, the factor becomes 2.17. In an alternative preferred embodiment of the present invention, the hydrogen index of different hydrocarbons can also be estimated using the expressions presented, for example, in "Schlumberger: Log Interpretation Principles/Applications," Schlumberger Educational Services, 1989, pp. 5–20 and 5–21, the content of which is expressly incorporated herein.

A simple power law has been found sufficient to fit published laboratory data for longitudinal relaxation time $T_1$ of methane gas, as well as log data. The expression used in accordance with the present invention is:

$$T_{1,g} = 25 \times 10^3 \rho/T^{1.17} \quad (5)$$

where $T_1$ is measured in seconds, the density $\rho$ in g/cm$^3$ and the absolute temperature T is in degrees Kelvin. Eq. (5) is valid for gas densities up to about 0.3 g/cm³; higher densities generally approaching a liquefied gas state.

In accordance with the present invention the non-wetting oil phase relaxes with its bulk relaxation $T_{1,o}$, which is determined, for example, by using viscosity measurements of a sample. It has been determined that in order to successfully detect liquid hydrocarbons, for the $T_1$-weighted measurements in accordance with the present invention a long $T_1$ component (low viscosity) on the order of 1–2 s is necessary. The relatively large values for the parameter $T_1$ of light hydrocarbons provide a mechanism for distinguishing these fluids from water, since $T_1$ of water in rocks is almost always less than about 500 msec. In partially hydrocarbon-saturated water wet rock the hydrocarbon-water contrast is even better because $T_1$ (and $T_2$) of water are shorter, due to the fact that water typically resides in the smallest pores.

Figure 5B:
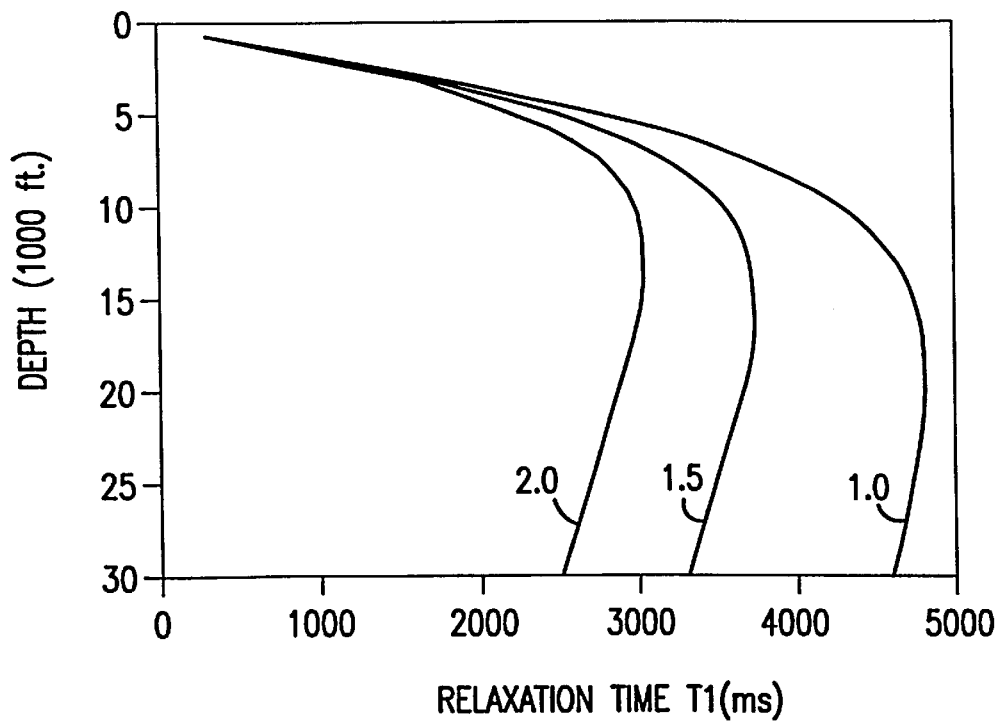
FIG. 5B shows the dependency of the longitudinal relaxation time $T_1$ as a function of depth at temperature gradients of 1, 1.5 and 2° F./100 ft, and pressure gradient of 43.3 psi/100 ft.
Figure 5C:
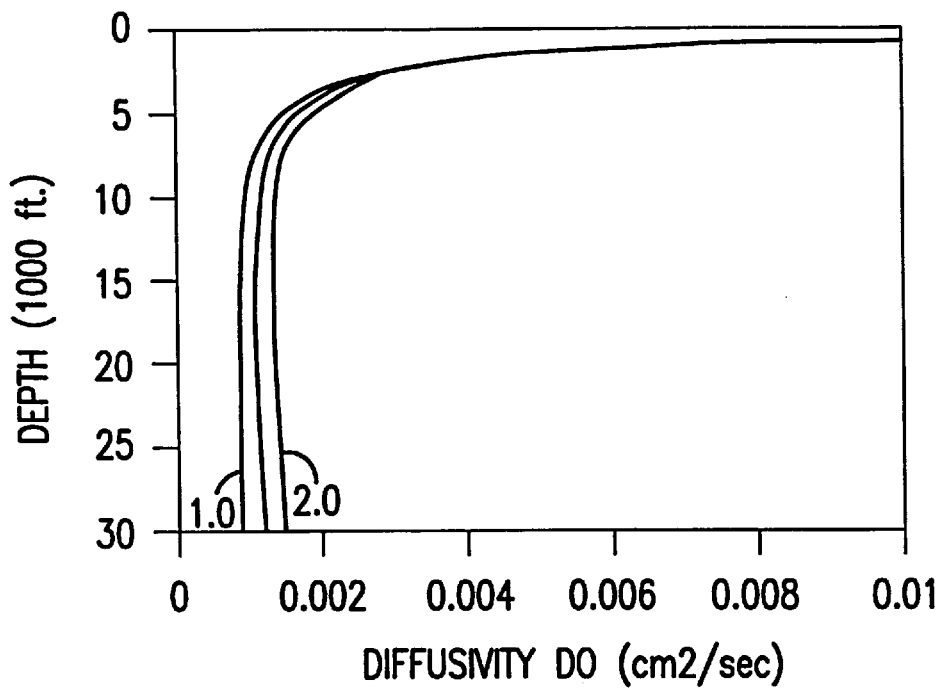
FIG. 5C shows the dependency of the self-diffusion coefficient $D_0$ of methane as a function of depth at temperature gradients of 1, 1.5 and 2° F./100 ft.
Figure 5D:
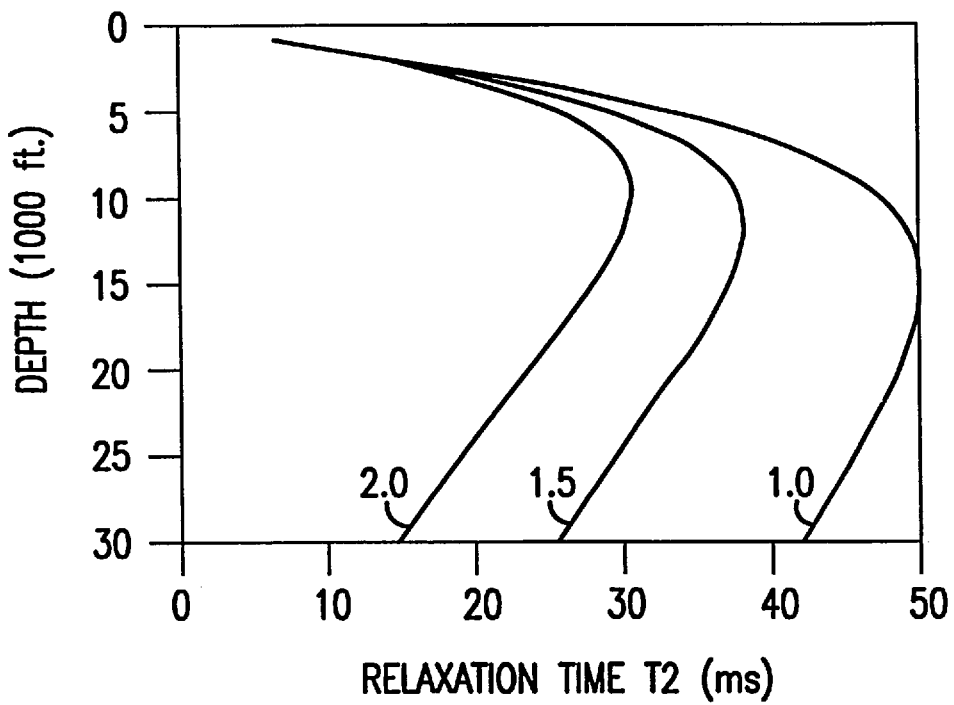
FIG. 5D shows the apparent transverse relaxation time $T_2^*$ based on diffusivity $D_0$ as in FIG. 5C, diffusion restriction $D/D_0$, and magnetic field temperature gradient of −0.18%/°C.
Figure 5E:
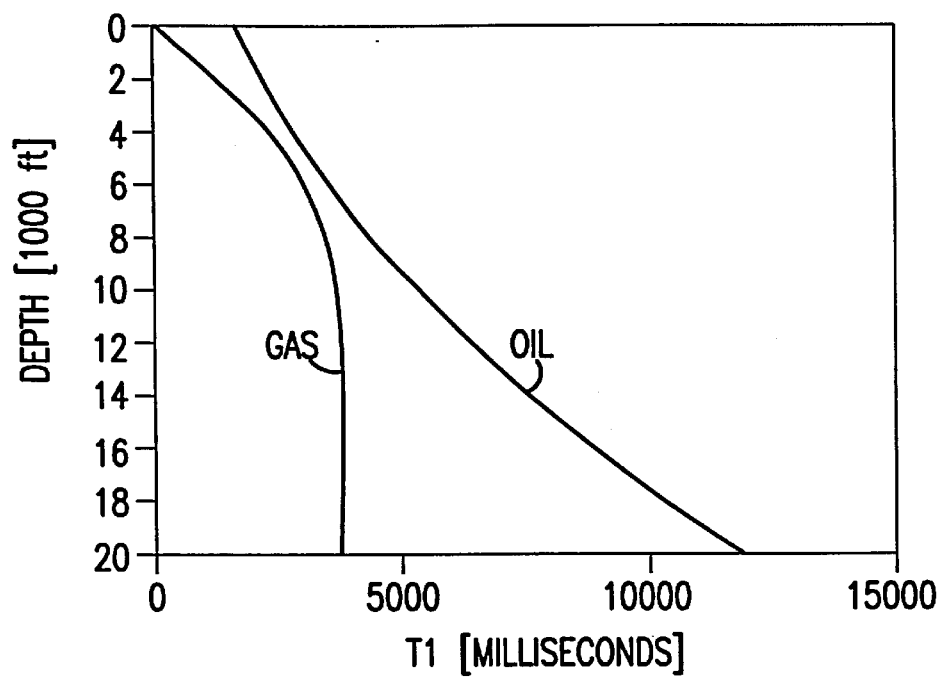
FIG. 5E shows values for the $T_1$ parameter of methane gas and light oils as a function of logging depth.

FIG. 5E shows, on the other hand, values for the $T_1$ parameter of gas (methane) and light oils at depths below 4000 feet. Both curves were computed assuming a geothermal gradient of $1.5_o$ F/100 feet. The oil curve was computed assuming a temperature-dependent viscosity, using the expression $\eta=\eta_0 \exp(Q/RT)$, where $\eta_o=0.01$ cp, Q=10.5 kJ/mol and R=8.314 J/mol/K. As seen in the figure, due to different relaxation mechanisms, $T_1$ for methane can be relatively short, i.e., between about 2.5 and 4 seconds, while in the specific example $T_1$ for oil can be very long (on the order of 10 sec). Standard logging practice requires to set the wait time between successive CPMG pulse trains long enough for substantially full recovery (about 95%) of the longitudinal magnetization. Accordingly, waiting times for a particular measurement have to be adjusted dependent on the specific oil.

The apparent diffusivity D of a fluid depends both on the self-diffusion coefficient $D_o$ and the restrictions imposed by the pore space. In accordance with a preferred embodiment of the present invention, an experimental temperature and density relationship for unrestricted gas diffusion $D_{0,g}$ is used, which can be expressed mathematically as:

$$D_{0,g}=8.5\times10^{-7}T^{0.9}/\rho, \quad (7)$$

where $D_{0,g}$ is measured in cm²/s, the temperature T is measured in degrees Kelvin and the density $\rho$ is expressed in g/cm³. Below 7,000 ft, the opposing effects of temperature and pressure stabilize the diffusion parameter $D_0$ at a value of about $10^{-3}$ cm²/s. Diffusion restriction in the pore space should also be taken into account since the diffusion length (given by sqrt($2\tau D_0$)) is approximately equal to 10 $\mu$m. $D/D_0$ ratios in rock samples at this length scale have been observed ranging from about 0.55 (Indiana limestone) to about 0.9 (oomoldic limestone). Sandstone samples have been found to cluster in a tight $D/D_0$ ratio range of 0.7–0.8, which is consistent with experimental observations of $T_{2,g}^\dagger$ from log data.

Because of diffusion, the intrinsic relaxation rate $1/T_{2,g}$ for gas is negligible compared to $1/T_{2,g}^\dagger$ (see Eq. (3)). Similarly, the diffusivity of the oil phase is small compared to that of the gas phase. consequently, the parameters $T_{2,o}$ and $T_{2,o}^\dagger$ which are used in the matched filter expression considered next are much larger than both $T_{2,g}^\dagger$ and also much larger than the total acquisition time required to separate oil from gas signals. As indicated above, numerical values for these parameters can be obtained, for example, from sample measurements.

Figure 5F:
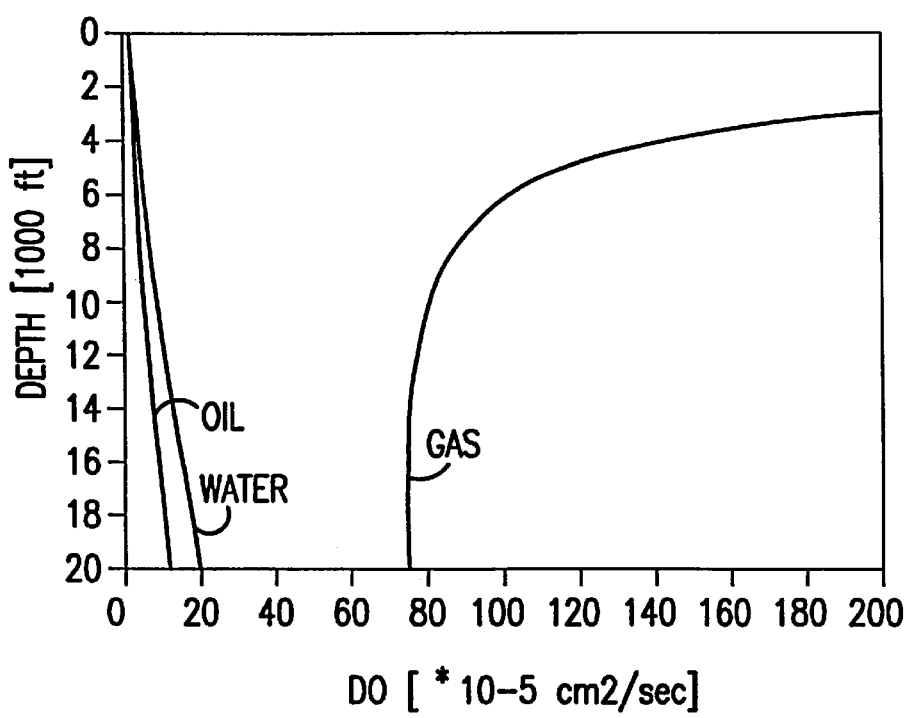
FIG. 5F illustrates the self diffusion coefficients $D_0$ for methane, water and light oil as a function of logging depth.
Figure 5G:
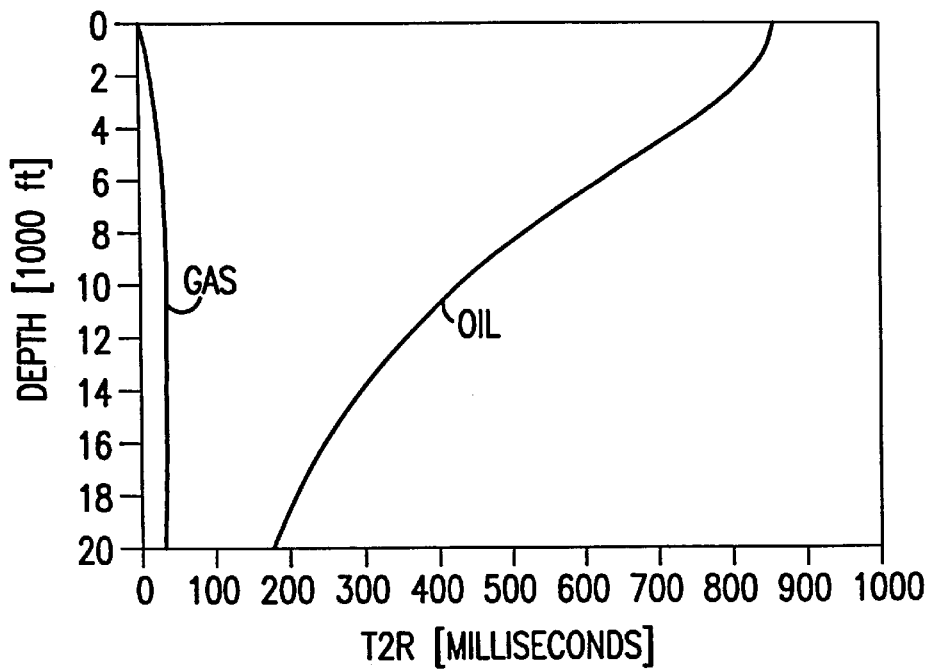
FIG. 5G illustrates the measured $T_{2R}$ for gas and oil as a function of logging depth.

FIG. 5F illustrates the self diffusion coefficients $D_0$ for methane, water and light oil. All curves are based on geothermal gradient of $1.5_0$ F/100 feet, and (for gas) a hydrostatic pressure. As seen, the methane $D_0$ is at least about 50 times larger than that of water and light oil. The resulting contrasts in the measured $T_2$ (i.e., $T_{2r}$) for gas compared to oil are shown in FIG. 5G. The plots include the effect of temperature and pressure on $T_1$ (see FIG. 5E) and D (see FIG. 5F) for both fluids and the effect of temperature on the parameter G for the tool. Moderate restriction diffusion effect on gas and no restriction effects on oil diffusion was assumed, i.e., $(D/D_0)_g=0.7$; $(D/D_0)_o=1$, Comparison of FIGS. 5E and 5G reveals that gas has a high ratio $T_1/T_2$ (larger than about 200) at all depths, which is a characteristic signature of gas. For light oil, however, this ratio is approximately equal to one and rises slowly with increased depth.

Table 2 summarizes expressions for the parameter estimates of different fluids used in accordance with a preferred embodiment of the present invention.

TABLE 2

| Fluid | Spin Lattice Relaxation (sec) | Self Diffusion coeff. (cm²/sec) | parameters/units |
|---|---|---|---|
| Methane | $T_{1,g} = 25.10^3\ \rho/T^{1.17}$ | $D_{0g} = 8.5.10^{-7}T^{0.9}/\rho$ | Gas density $\rho$ in gramm/cc; T- abs temp in Kelvin |
| Oil | $T_{1,o} = 1.2(T/298)/\eta$ | $D_{0,o} = 1.3(T/298)/\eta$ | $\eta$ is oil viscosity in cp; T- abs temp in Kelvin |
| Water | $T_{1,w} = 3(T/298)/\eta$ | $D_{0,w} = 1.2(T/298)/\eta$ | Same as above |

For illustrative purposes, examples of pre-calculated values for $HI_g$ diffusivity and the relaxation time parameters $T_{1,g}$ and $T_{2,g}^\dagger$ as functions of depth are shown in FIGS. 5A to 5D. In particular, FIG. 5A shows the hydrogen index (HI) of methane as a function of depth at different temperature gradients; FIG. 5B shows the dependency of the longitudinal relaxation time $T_1$ as a function of depth at temperature gradients of 1, 1.5 and 2° F./100 ft, and pressure gradient of 43.3 psi/100 ft; FIG. 5C shows the dependency of the self-diffusion coefficient $D_0$ of methane as a function of depth; and FIG. 5D shows the apparent transverse relaxation time $T_2^\dagger$ based on diffusivity $D_0$ as in FIG. 5C, diffusion restriction $D/D_0$, and magnetic field temperature gradient of $-0.18\%$ /°C.

In the examples shown in FIGS. 5A–D, a hydrostatic pressure gradient of 43.3 psi/100 ft and temperature gradients of 1; 1.5 and 2° F./100 ft were assumed, as shown. Additional parameters used in the examples include: frequency=720 kHz, $\tau_{eff}=0.65$ ms and $D_g/D_{0,g}=0.8$. The tool and the formation temperature were assumed to be equal. It can be seen from FIGS. 5B and 5D that functionally the curves for $T_1$ and $T_2^\dagger$ are similar and that the ratio $T_1/T_2^\dagger$ stays within narrow limits for a wide range of temperatures and logging depth.

Data Acquisition

Figure 6:
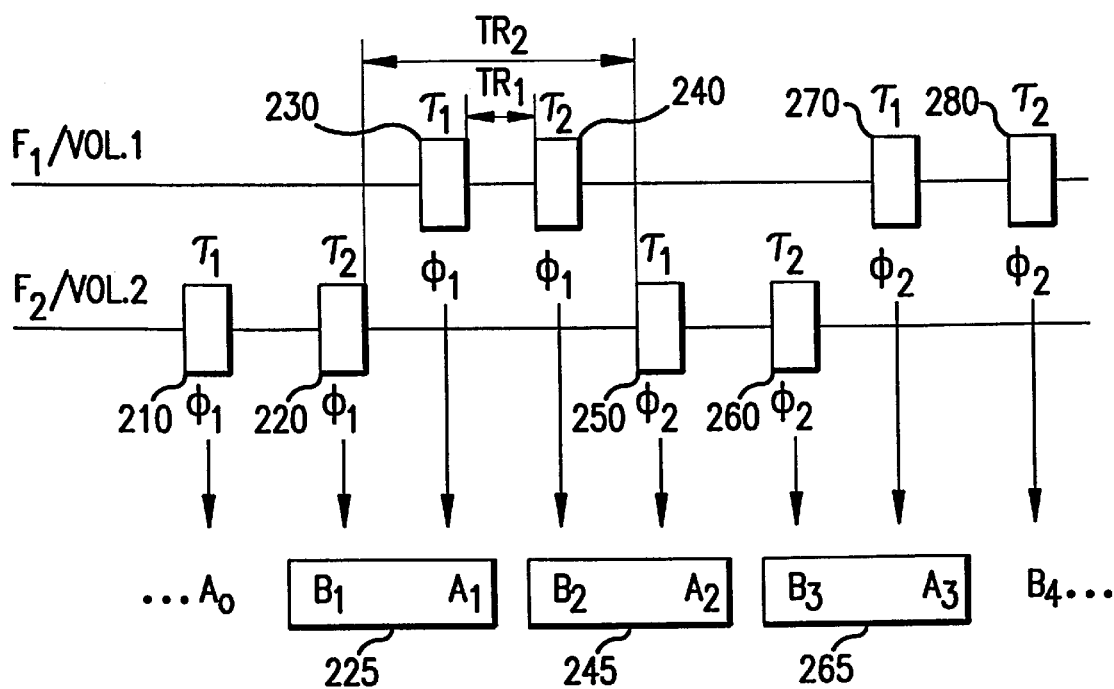
FIG. 6 is an illustration of an interleaved data acquisition pulse sequence for $T_1$ weighted and diffusion-weighted saturation recovery CPMG echo trains in a specific embodiment of the present invention using two tool frequencies.

As indicated above, the MRIL tool of the present invention is capable of performing separate, quasi-simultaneous measurements in different sensitive volumes by simply switching the operating frequency of the tool by a small amount. In accordance with a preferred embodiment of the present invention, this multi-frequency capability of the MRIL tool is used to provide a new data acquisition method which is particularly suitable for the detection of gas on the basis of NMR measurements with different recovery times $T_{Ri}$. To this end, with reference to FIG. 6, a novel interleaved pulse sequence is proposed in which at least two CPMG pulses 210 and 220 associated with resonant frequency $F_2$ are followed by at least two CPMG pulses 230, 240 associated with a different resonant frequency $F_1$. As shown in FIG. 6, the NMR measurement is continued next using at least two new pulses 250, 260 at the initial resonance frequency $F_2$, followed by at least two separate pulses 270, 280 at the $F_1$ frequency. Due to the fact that resonant frequency $F_1$ excites protons only in volume 1 of the formation and resonant frequency $F_2$ excites protons only in volume 2 of the formation, pairs 225, 245, 265, etc., of independent complex data points can be collected at each depth mark. As shown for illustrative purposes in FIG. 6, the first data point in each pair, generally designated as $B_i$, corresponds to a short recovery time $T_{R1}$, while the second data point, generally designated as $A_i$, corresponds to a long recovery time $T_{R2}$.

Thus, using the data acquisition sequence illustrated in FIG. 6, by "hopping" the resonance frequency $F_i$ of the tool, and alternating between adjacent resonant volumes of the formation one can obtain a sequence of signal pairs, each pair corresponding to substantially the same depth mark in the formation, but measured at different recovery times. It should further be noted that data for two different recovery times need not necessarily be obtained from only two different frequencies. For example, two or more measurements associated with different frequencies can be combined (i.e., averaged) to result in a single data stream corresponding to either a short, or a long recovery time. Furthermore, it should be clear that by using more than two resonance frequencies, and applying a correspondingly larger number of pulses in each resonant volume, the data acquisition method of the present invention can easily be extended to the more general case of M-tuple measurement data sets, each measurement point corresponding to a different recovery time $T_{Ri}$.

The interleaved multi-frequency data acquisition method described above is clearly preferable to prior art methods which require separate logging passes, because it provides a simple approach to dealing with depth alignment problems. Preferably, the pulse sequences in FIG. 6 systematically alternate the roles of all sensitive volumes (and pulse phases) in order to negate any systematic difference between operating frequencies.

The data acquisition method was described above with reference to identical CPMG sequences, which mode is referred to in the present application as $T_1$-weighted acquisition. Data from this acquisition mode is suitable for the Differential Spectrum Method (DSM) described in the Akkurt et al paper. Notably, however, the method is also suitable for direct signal subtraction in the time domain, as described in more detail next.

In an alternative preferred embodiment of the present invention, a novel data acquisition mode referred to as $T_1$- and diffusion-weighted acquisition can also be used. As indicated above with reference to the SSM method discussed in the Akkurt et al. paper, the contrast between liquid and gas signals can be enhanced by using a slightly larger pulse-echo spacing for the CPMG train associated with the shorter recovery interval. This embodiment is illustrated in FIG. 6 using two different intervals $\tau_i$ for each successive pulse in the same resonance volume. It has been found, however, that it is not necessary to eliminate the gas signal altogether. For example, an increase by only 40% in the pulse echo $\tau$ has been found to cause a 50% decrease in the diffusion-induced part of $T_2$. As indicated above with reference to the SSM method, because of diffusion dominance, the effect is much more pronounced for gases than for liquids, and can accordingly be used to enhance the separation of the two phases.

Signal Processing

The method for fluid detection in accordance with a preferred embodiment of the present invention assumes data acquisition in the presence of a static magnetic field gradient in the range 10–30 G/cm. The method further requires at least two separate measurements with different saturation-recovery times $T_{Ri}$ and/or different echo-to-echo spacings, and is implemented using the data acquisition sequence illustrated in FIG. 6. In addition, the very low signal-to-noise (SNR) levels which are due to HI losses and incomplete magnetization recovery in a typical NMR measurement necessitate signal detection using two-channel complex data stream. Therefore, in a preferred embodiment of the present invention data is acquired in two orthogonal channels, and averaged over a vertical logging interval to increase the SNR for the acquired measurement data.

Figure 7:
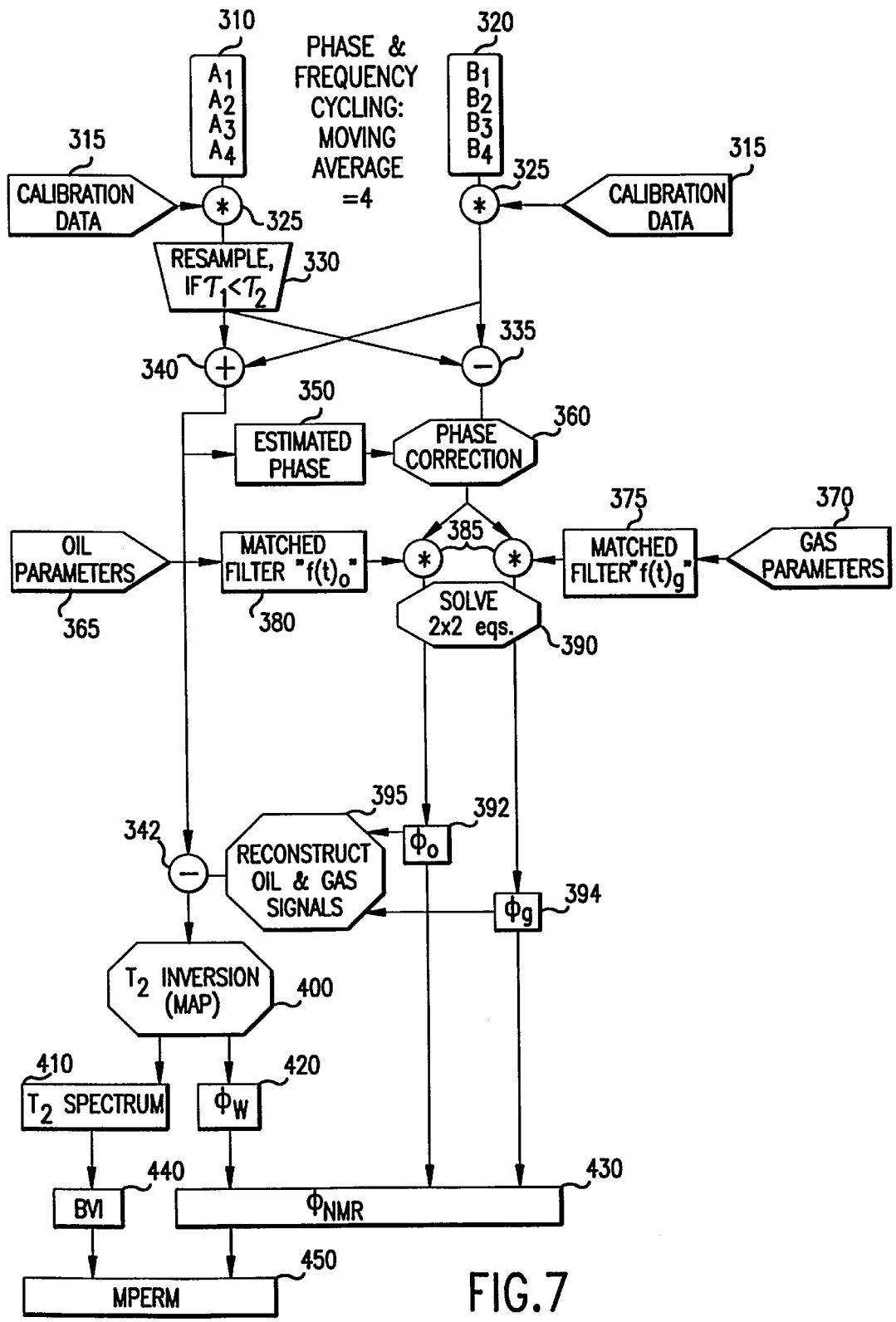
FIG. 7 is a flow diagram of the data processing method in accordance with a preferred embodiment of the present invention.

Turning next to FIG. 7 it shows in semi-block diagram form the signal processing method in accordance with a preferred embodiment of the present invention. Specifically, the determination of water, oil and gas saturations in the sensitive volume begins by performing at least two interleaved $T_1$-weighted measurements to separate the wetting phase (brine, surface-dominated relaxation) from the non-wetting phase (light hydrocarbons, bulk-dominated relaxation). Optionally, these measurements can be diffusion-weighted as well. As shown in FIG. 7, this results in two parallel data sets of complex time-domain data. Data sequence 310 generally corresponds to data obtained from the long recovery time $T_{R2}$, while data sequence 320 corresponds to data obtained from the short recovery time $T_{R1}$. Between about 150 and 300 data points are used in each sequence. Preferably, the recovery times used are about 2 sec for $T_{R1}$ and about 8 sec for $T_{R2}$. Pairs of echo trains are formed by matching overlapping short and long TR intervals thereby minimizing the systematic variations introduced when formation bed boundaries are crossed.

Figure 8A:
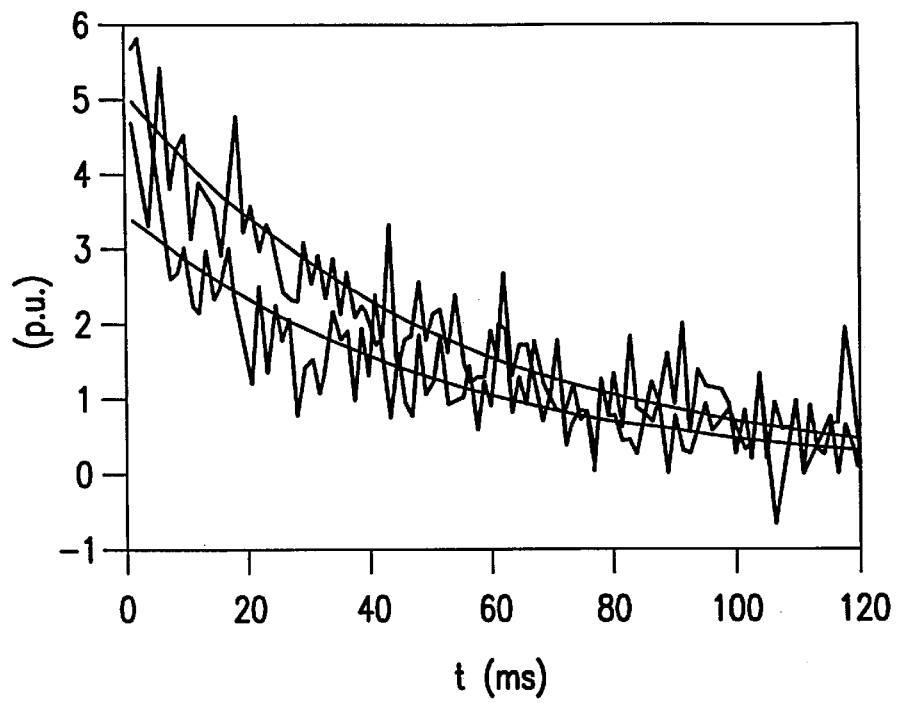
FIG. 8A illustrates the difference between two signals with different recovery times $TR_i$.

Following the data acquisition process, in block 325 the two data sets are corrected using calibration data from blocks 315. Specifically, such calibration data is obtained from samples at room temperature, with 100% water saturation, for example in a water-filled tank. FIG. 8A shows two such calibrated data sequences as functions of time. As shown in FIG. 8A, the magnitude values for the measurement signals are conveniently calibrated in porosity units (p.u.). Skipping for a moment block 330, next the complex difference between the signals in each data pair is obtained in subtractor 335 to eliminate the brine contribution; the sum signal is obtained in adder 340 to estimate the input signal phase and phase-correct the difference signal in block 335 accordingly. Specifically, it has been observed that while the absolute phase of the NMR signal is subject to slow variations due to hole and tool conditions, it shows excellent short-term stability. Therefore, the phases of the sum and the difference signals are approximately equal. In accordance with the present invention this feature is used to correct the phase of the difference signal on the basis of a phase estimate for the sum signal which was found to be comparatively more accurate.

In particular, a depth-averaged signal phase is computed in block 350 from the complex sum signal. If proper frequency and phase cycling has been employed during data acquisition, all sum and difference echoes have the same average phase. The phase estimated in block 350 is used to rotate, in phase correction block 360, the phase of all data points in the complex difference signal into the real axis. Such rotation yields the true absorption mode (real-valued) signal component The dispersion signal component (imaginary valued) can be discarded.

Based on the parametric representations for relaxation times and diffusion characteristics of the non-wetting hydrocarbon phases which are computed, as indicated in the section "Signal Modeling and Corrections", and stored in block 365 for the oil and block 370 for the gas components. Matched filters representing the liquid and the gaseous phases are computed next in blocks 375, 380 in the echo-time domain, using the expressions:

$$f(t)_o = [exp(-TR_1/T_{1,o}) - exp(-TR_2/T_{1,0})]exp(-t/T_{2,o}), \quad (7a)$$

$$f(t)_g = HI_g[exp(-TR_1/T_{1,o}) - exp(-TR_2/T_{1,o})]exp(-t/T_{2,o}^\dagger) \quad (7b)$$

where all used parameters have been pre-computed.

In general, the filter functions in Eqs. (7a–7b) are not orthogonal and cannot be directly applied to the data. (See FIG. 9A) Instead, the amplitude responses to these filters are extracted from the phase-corrected difference signal d(t) by solving, in block 390, the overdetermined equation system, $$Ax = d(t), A = [f(t)_o^T f(t)_g^T] \quad (8)$$

in a least-squares sense. The solution is found by solving the following 2x2 equation system for the amplitude vector x:

$$(A^TA)x = A^T d(t), \quad (9)$$

If the difference signal d(t) was properly scaled in p.u., the first element of the solution vector x is oil-filled porosity $\Phi_o$, obtained in block 392, and the second is gas-filled porosity $\Phi_g$ (block 394). Calculating backwards from these numbers, the properly scaled oil and gas signatures can be reconstructed in block 395, and subtracted from the complex sum signal in block 342. The remainder is the signal originating from brine, which, as wetting phase, is sensitive to the surface-to-volume ratios in the remaining pore space available to water.

In block 400, a $T_2$ inversion mapping is constructed, as discussed, for example in the Prammer et al. paper above. The results are used, in block 410, to estimate the $T_2$ spectrum of the signal and in block 420 to estimate the water-bound porosity.

These ratios are indicative of the non-producible water volume held in place by capillary forces (BVI), which is computed in block 440. On the other hand, the total area under the $T_2$ curve is interpreted as water-filled porosity $\Phi_w$ which is computed in block 420. The total NMR porosity can be computed in block 430 using the expression:

$$\Phi_{NMR} = \Phi_W + \Phi_o + \Phi_g \quad (10)$$

The free-fluid index as seen from the water phase is augmented by oil and gas porosity:

$$FFI = FFI_W + \Phi_o + \Phi_g \quad (11)$$

From $\Phi_{NMR}$, BVI and FFI, a permeability estimate can be calculated in block 450 which depends only on NMR-derived quantities.

Processing of diffusion-weighted data.

Turning back to block 330 in FIG. 7, for a diffusion-weighted measurement a complication arises from the different sampling grids employed in acquiring the data sets which make up a data pair. In this case, data from the shorter echo spacing is mapped onto the wider sampling grid by linear interpolation between complex echoes. Diffusion-weighting is taken into account to give the following matched-filters expressions:

$$f(t)_o = [exp(-TR_1/T_{1,o}) - exp(-TR_2/T_{1,o})]exp(-t/T_{2,o}), \quad (12a)$$

$$f(t)_g = HI_g[1 - exp(-TR_2/T_{1,g})]exp(-t/T_{2,g}^\dagger) - HI_g[1 - exp(-TR_1/T_{1,g})] \\ exp(-t/T_{2,g}^\dagger(\tau_2/\tau_1)^2) \quad (12b)$$

The diffusion-weighted data is next processed following the flow graph in FIG. 7. The combined $T_1$-weighted and diffusion-weighted measurement is advantageously used in cases where the gas filled porosity and HI are relatively low, and correspondingly the SNR of the measurement is relatively low.

Error estimates for $T_1$-weighted and diffusion-weighted data acquisitions in accordance with a preferred embodiment of the present invention can be obtained using the following considerations The input data consists of two data sets, weighed by different recovery times and possibly sampled with different echo spacings Each set is individually calibrated for HI=1.0. To compute the uncertainty of the parameter estimates, it is assumed that the noise in each data set is random and has Gaussian distribution with standard deviation $\sigma=\sqrt{2}$. As indicated in blocks 350 and 360 above, a depth-averaged signal phase is computed from the complex second echo in the sum. The estimated phase is used to rotate all complex differences into the real axis. Allowing for a small error in phase estimation, the noise component in the real-valued difference signal (dt) is approximately 1.5 p.u. Gas and oil porosities are given as least-squares solutions in block 390 in FIG. 7. Formally, the least-squares solution can be written as:

$$x_{(LSQ)} = (A^TA)^{-1}A^T d(t) \quad (13)$$

Figure 10:
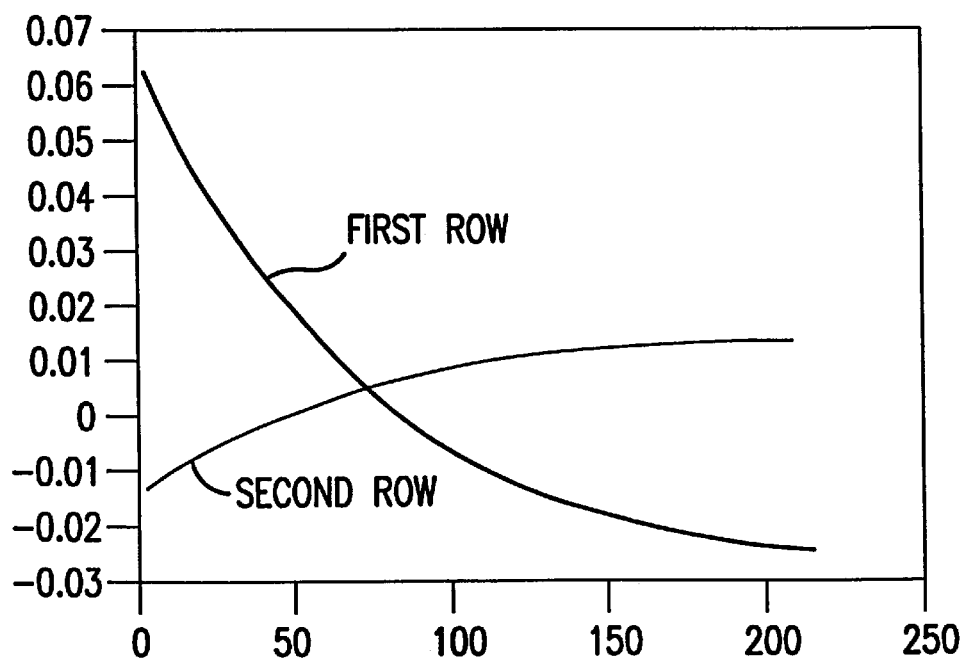
FIG. 10 shows orthogonalized filter functions of the gas and the oil matched filters in accordance with the resent invention.

The sensitivity of the solution to random errors in the input is given by the condition number of the square, positive-definite matrix $A^TA$. The orthogonalized oil-sensitive filter function $f(t)'_o$, is the first row of the expression $(A^TA)^{-1}A^T$. The second row of this expression contains the orthogonal filter $f(t)'_g$, which is sensitive to the gas component. The orthogonal filter responses are shown in FIG. 10. Filter response functions are computed as follows:

$$\Phi_o = \int_0^\infty d(t)(f(t))'_o dt$$

$$\Phi_g = \int_0^\infty d(t)(f(t))'_g dt$$

The average output uncertainty was determined by Monte Carlo simulation. Using 100,000 samples, and assuming parameters, $HI_g=0.5$, $T_{1,g}=5$ s, the standard output deviation in the answer for gas filled porosity is $\approx 2.5$ p.u. The uncertainty in oil-filled porosity is substantially reduced and is approximately equal to 1 p.u., dependent on $T_{1,o}$.

For the reader's convenience, a list of all notations used in the description above is given next.

Nomenclature

A=design matrix for least-squares problem
$A^T$=transpose matrix of A
BVI=bulk volume irreducible water, p.u.
D=restricted diffusivity, $cm^2/S$
$D_o$=unrestricted diffusivity, $cm^2/S$
d(t)=difference function
f(t)=filter function
FFI=free fluid index, p.u.
G=magnetic field gradient, G/cm
HI=hydrogen index, relative to water
MPHI=apparent NMR porosity, p.u.
T=absolute temperature, °K $T_1$=longitudinal relaxation time, s
$T_1^\dagger$=pseudo transverse relaxation time, s
$T_2$=transverse relaxation time, s
$T_2^\dagger$=apparent transverse relaxation time, s
TE=CPMG echo-to-echo delay (TE=2τ); s
TR=recovery time, s
x=solution vector to least-squares problem
Φ=porosity, p.u.
$\Phi_{NMR}$=corrected NMR porosity, p.u.
$\Phi_n$=CPMG phase, n=1 or 2
γ=gyromagnetic ratio, rad$^{-1}$G$^{-1}$
Σ=density, g/cm$^3$
σ=standard deviation
τ=CPMG pulse-to-echo delay (τ=TE/2), s
$\tau_{eff}$=diffusion-effective CPMG delay, s
Subscripts
  g=gas
  o=oil The following figures serve to provide better understanding of different aspects of the invention with reference to signals obtained in different processing blocks in FIG. 7.

Figure 8B:
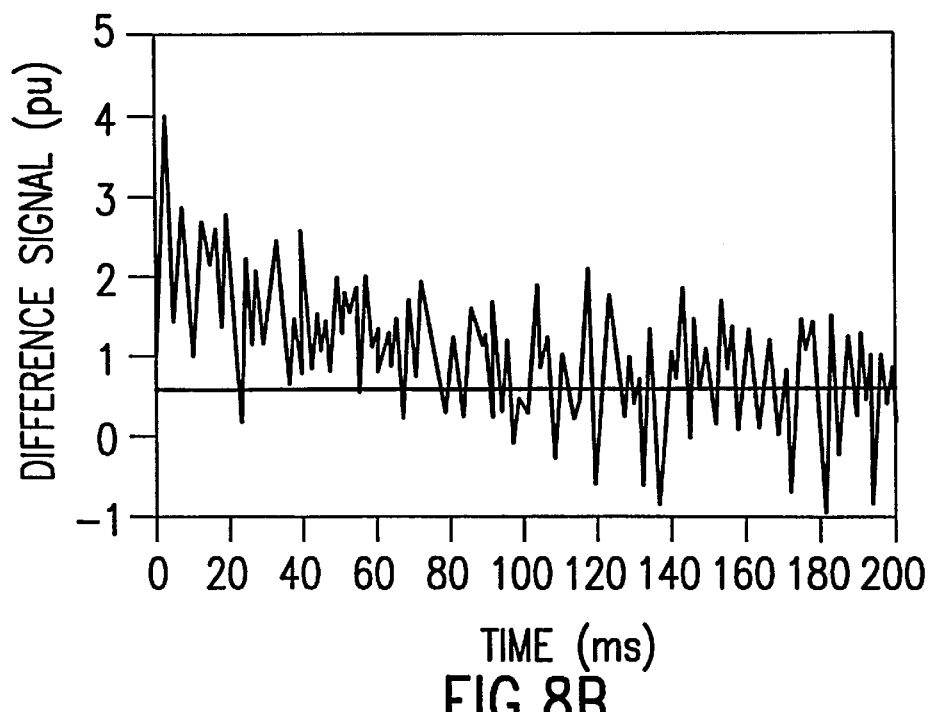
FIG. 8B shows a sample display of a difference data signal acquired at depth 15710 ft, as a function of time.
Figure 8C:
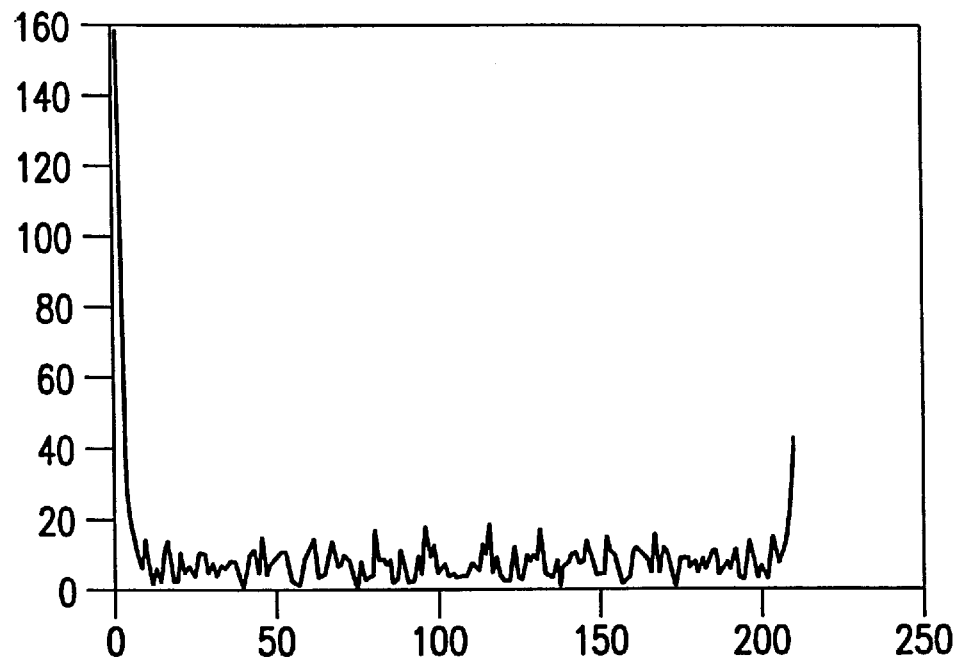
FIG. 8C is the magnitude of the Fourier transform of the signal shown in FIG. 8B.

In particular, FIG. 8A illustrates the difference between two signals with different recovery times $TR_i$. FIG. 8B shows a sample display of a difference data signal obtained at depth 15710 ft, as a function of time. FIG. 8C is the magnitude of the Fourier transform of the signal shown in FIG. 8B.

Figure 9A:
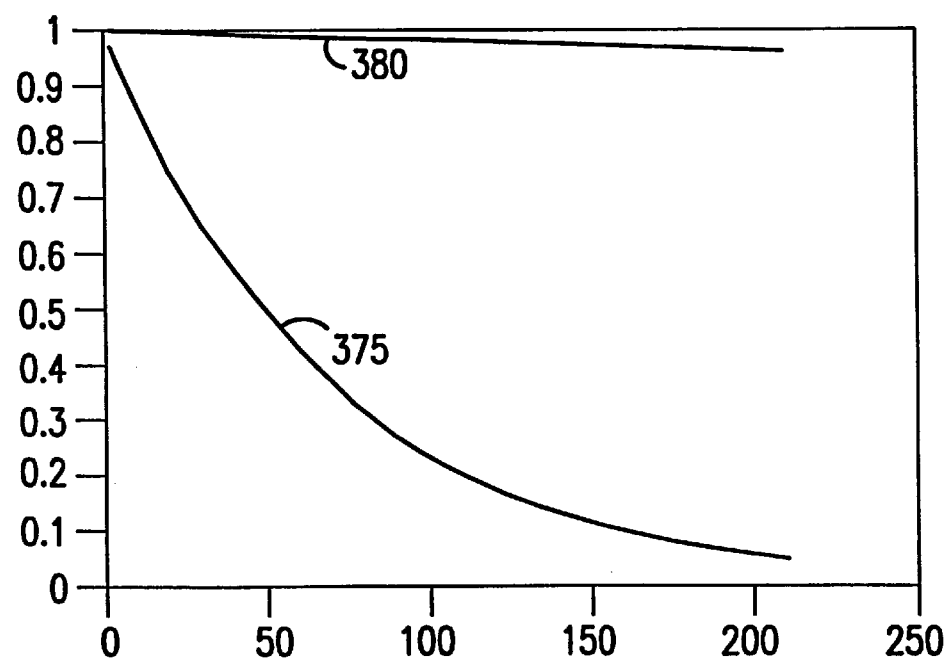
FIG. 9A shows sample response of the gas and the oil matched filters in accordance with the present invention.
Figure 9B:
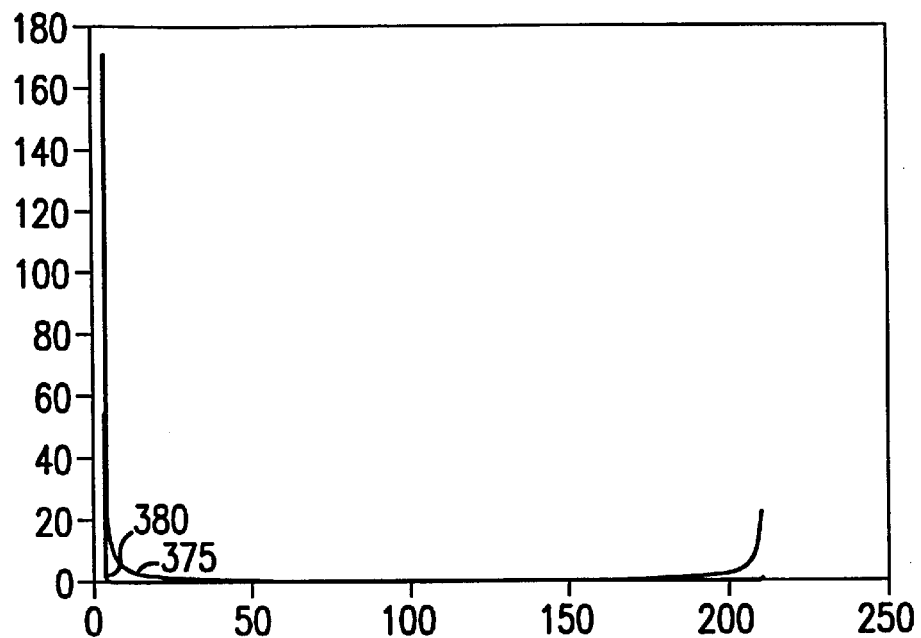
FIG. 9B is the magnitude of the Fourier transform of the matched filter responses shown in FIG. 9A.

FIG. 9A shows the response of the gas (block 375) and the oil (block 380) matched filters in accordance with the present invention; FIG. 9B illustrates the magnitude of the Fourier transform of the matched filters responses shown in FIG. 9A.

FIG. 10 shows the orthogonalized filter functions of the gas and the oil matched filters in accordance with the present invention.

Results

Logging tests were performed in single-frequency and dual frequency operating modes to assess the amount of vertical and lateral motion, which could affect the accuracy of the $T_1$-weighted measurements conducted in accordance with the present invention. A similar operating procedure was already in place to set the optimum delay time between measurements in the pay zone. Data acquired under a variety of hole conditions and $T_1$ values were examined; logging speeds in this particular mode were typically 300 ft/hr. In all cases, increasing the recovery time interval resulted either in a monotonic increase in NMR amplitude or in no increase. Sudden increases in amplitude at short recovery intervals, indicative of uncontrolled tool motion, were not observed.

The effect of invasion was studied by comparing results from wells drilled with water-base muds (WBM) and oil-muds (OBM). The WBM-drilled formations generally suffer high invasion and residual oil and gas saturations are low. Nevertheless, in many cases gas quantities above the detectability threshold are present, possibly due to backsaturation of gas into the invaded zone. As indicated above, another factor aiding the MRIL® is the 4" blind zone into the formation. OBM filtrate generally invades less and is therefore better suited for near-borehole saturation measurements. Oil filtrate mixes with the connate oil and replaces it to a certain extent. Because the filtrate has low viscosity, OBM aids the described hydrocarbon detection method by supplying a slowly relaxing component with known $T_1$. We recommend performing $T_1$ and $T_2$ measurements of filtrates in the laboratory at 1 MHz to assess the effect of OBM invasion.

The following example data was acquired in a deep (>10,000 ft), on-shore gas well, drilled with OBM. The gas parameters are summarized in Table 3.

TABLE 3

| parameters for example data | |
|---|---|
| gas temperature: | 100° C. |
| gas pressure: | 9000 psi |
| gas type: | CH$_4$ |
| CH$_4$ density: | ρ = 0.26 g/cm$^3$ |
| CH$_4$ hydrogen index: | HI$_g$ = 0.6 |
| longitudinal relaxation time: | $T_1$ = 6s |
| unrestricted diffusivity: | $D_0$ = 0.7 x 10$^{-3}$cm$^2$/s |
| diffusion restriction (est.): | $D/D_0$ = 0.8 |
| magnetic field gradient | G = 18 G/cm |
| effective pulse-echo spacing: | $\tau_{eff}$ = 0.65 ms |
| apparent transverse relaxation: | $T_2^\dagger$ = 60 ms |
| $T_1/T_2^\dagger$ contrast: | ~100 |

Figure 11:
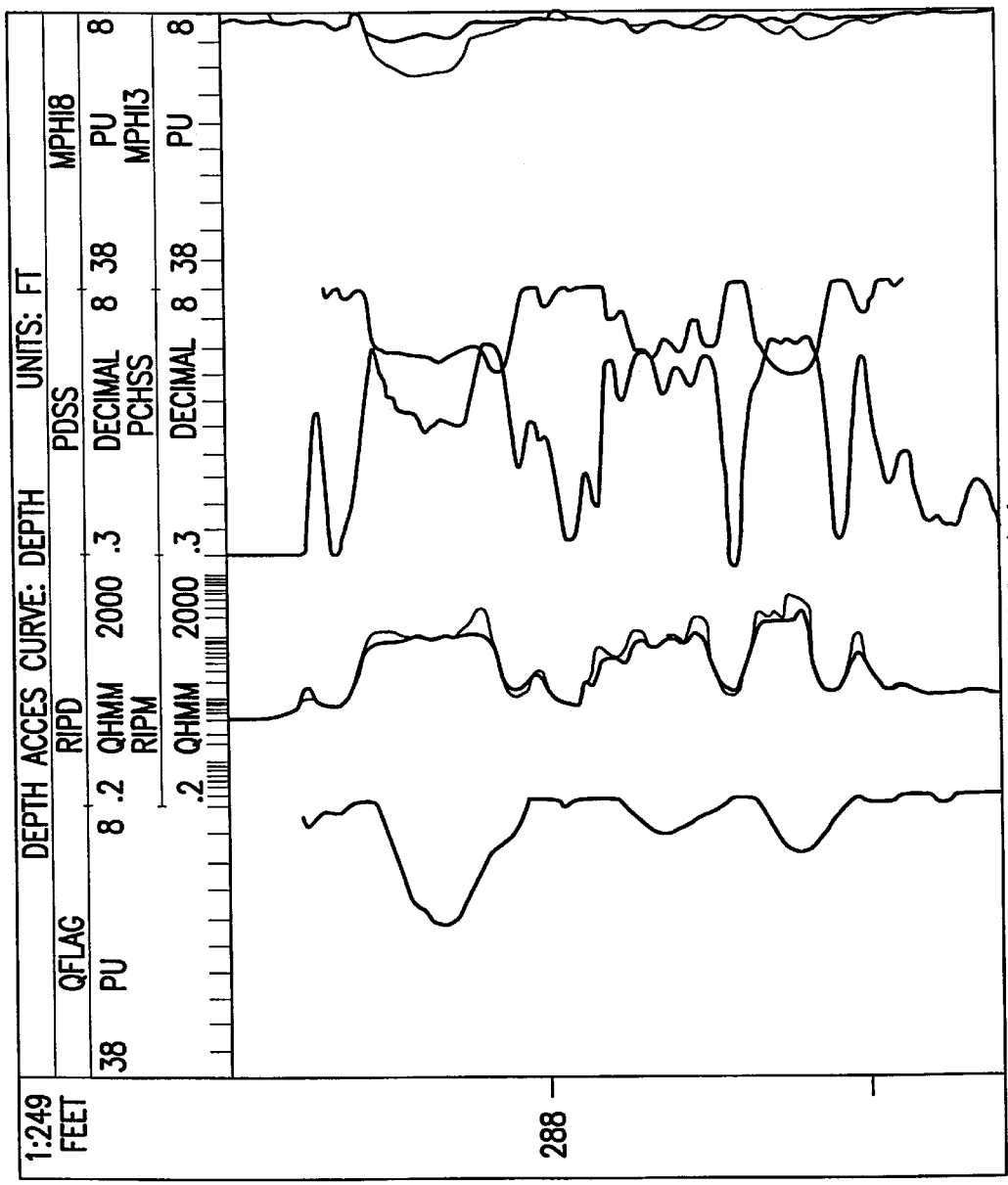
FIG. 11 shows logging data from an off-shore gas well at depth>10,000 ft.

Log results are shown in FIG. 11. For the example illustrated in FIG. 11 NMR data for recovery times of $TR_1$=3 s and $TR_2$=8 s were acquired in separate passes with a pulse-echo spacing τ=0.6 ms. Both apparent NMR porosities are too low in the gas zone (shown in track 4). Complex echo sums and differences from these echo sets were computed. The sum had a constant phase of −2.1 rad, which was used to convert the difference signal to real-type values. Matched filters for the oil component:

$HI_o$=1.0, $T_{1,o}$=2000 ms, $T_{2,o}$=100 ms;

and for the gas component:

$HI_g$=0.6, $T_{1,g}$=6000 ms, $T_{2,g}^\dagger$=60 ms;

were computed and applied to the data in a least-squares sense as described above. The oil-filter response was essentially zero (not shown), the gas-filter response is plotted in track 1.

Gas-corrected NMR porosity indicates that mud filtrate did not invade the sampling diameter (15" at a probe temperature of 100° C.), or that gas did backsaturate into the invaded zone. In either case, the results clearly indicate the value of hydrocarbon saturation measurements near the borehole wall.

While the invention has been described with reference to a preferred embodiment, it will be appreciated by those of ordinary skill in the art that modifications can be made to the structure and form of the invention without departing from its spirit and scope which is defined in the following claims.

What is claimed is:

1. A method for determination of petrophysical properties of a geologic formation using NMR logging measurements comprising the steps of:
   providing a first set of CPMG pulses associated with a first recovery time $TR_1$;
   providing a second set of CPMG pulses associated with a second recovery time $TR_2$;
   receiving NMR echo signals in response to said first and said second set of CPMG pulses;
   combining data representing NMR echo signals received in response to pulses in said first set and data representing NMR echo signals received in response to pulses in said second set to form a composite signal comprising data pairs, each pair corresponding to substantially the same depth mark in the formation; wherein one element of the data pair is associated with the first recovery time and a second element of the data pair is associated with the second recovery time; and
   determining petrophysical properties of the geologic formation on the basis of the generated difference signal.

2. The method of claim 1 wherein said second recovery time $TR_2$ is longer than said first recovery time $TR_1$.

3. The method of claim 1 wherein the first set of CPMG pulses is associated with a pulse echo spacing $\tau_1$ and the second set of CPMG pulses is associated with a pulse echo spacing $\tau_2$ shorter than $\tau_1$.

4. The method of claim 2 wherein the first set of CPMG pulses is associated with a pulse echo spacing $\tau_1$ and the second set of CPMG pulses is associated with a pulse echo spacing $\tau_2$ shorter than $\tau_1$.

5. The method of claim 2 further comprising the step of removing signal components associated with a water phase in the formation by generating a difference signal, wherein said difference signal is generated by pair-wise subtraction of the elements of the composite signal.

6. The method of claim 5 further comprising the step of identifying signal components associated with a liquid phase of the formation by passing said difference signal through a first matched filter having response which is matched to expected parameters of the liquid phase.

7. The method of claim 6 wherein the first matched filter $f(t)_o$ is given by the expression:

$$f(t)_o = [exp(-TR_1/T_{1,o}) - exp(-TR_2/T_{1,o})]exp(-t/T_{2,o})$$

where $T_{1,o}$ is the longitudinal relaxation time of the liquid phase; and $T_{2,o}$ is the transverse relaxation time of the liquid phase.

8. The method of claim 5 further comprising the step of identifying signal components associated with a gaseous phase of the formation by passing said difference signal through a second matched filter having response which is matched to expected parameters of the gaseous phase.

9. The method of claim 8 wherein the second matched filter $f(t)_g$ is given by the expression:

$$f(t)_g = HI_g[exp(-TR_1/T_{1,o}) - exp(-TR_2/T_{1,o})]exp(-t/T_{2,o}^\dagger)$$

where $HI_g$ is the hydrogen index of the gas phase; $T_{1,o}$ is the longitudinal relaxation time of the liquid phase; and $T_{2,o}^\dagger$ is the apparent transverse relaxation time.

10. The method of claim 5 further comprising the steps of:

providing a first matched filter having response which is matched to expected parameters of the liquid phase; wherein the first matched filter $f(t)_o$ is given by the expression:

$$f(t)_o = [exp(-TR_1/T_{1,o}) exp(-TR_2/T_{1,o})]exp(-t/T_{2,o}),$$

in which $T_{1,o}$ is the longitudinal relaxation time of the liquid phase; and $T_{2,o}$ is the transverse relaxation time of the liquid;

providing a second matched filter having response which is matched to expected parameters of the gaseous phase;

wherein the second matched filter f(t)g is given by the expression:

$$f(t)_g = HI_g[exp(-TR_1/T_{1,o}) - exp(-TR_2/T_{1,o})]exp(-t/T_{2,o}^\dagger),$$

in which $HI_g$ is the hydrogen index of the gas phase; $T_{1,o}$ is the longitudinal relaxation time of the liquid phase; and $T_{2,o}^\dagger$ is the apparent transverse relaxation time;

solving the matrix equation $A x=d(t)$ where $A=[f(t)_o f(t)_g]$; d(t) is the difference signal scaled in porosity units, and x is a solution vector, the first element of which is hydrogen liquid-filled porosity $\Phi_o$, and the second is gas-filled porosity $\Phi_g$.

11. The method of claim 10 further comprising the steps of:

reconstructing a liquid phase signal component on the basis of the solution vector x and the first matched filter $f(t)_o$;

reconstructing a gaseous phase signal component on the basis of the solution vector x and the second matched filter $f(t)_g$;

subtracting said liquid phase signal component and said gaseous phase signal component from a sum signal generated by pair-wise addition of the elements of the composite signal to obtain a water phase signal; and estimating water bound porosity $\Phi_W$ on the basis of the water phase signal.

12. The method of claim 11 further comprising the step of estimating the bound volume irreducible (BVI) on the basis of the water phase signal.

13. The method of claim 12 further comprising the step of estimating the total NMR porosity using the expression:

$$\Phi_{NMR} = \Phi_W + \Phi_o + \Phi_g.$$

14. The method of claim 12 further comprising the step of estimating the free-fluid index FFI using the expression:

$$FFI = FFI_W + \Phi_o + \Phi_g.$$

15. The method of claim 14 wherein the step of determining petrophysical properties of the geologic formation comprises the steps of computing the NMR permeability on the basis of the BVI and the $\Phi_{NMR}$ estimates.

16. The method of claim 3 further comprising the steps of:

mapping data from first set onto a sampling grid corresponding to data from the second set prior to the step of forming a composite signal;

removing signal components associated with a water phase in the formation by generating a difference signal, wherein said difference signal is generated by pair-wise subtraction of the elements of the composite signal;

providing a first matched filter having response which is matched to expected parameters of the liquid phase; wherein the first matched filter $f(t)_o$ is given by the expression:

$$f(t)_o = [exp(-TR_1/T_{1,o}) - exp(-TR_2/T_{1,o})]exp(-t/T_{2,o}),$$

in which $T_{1,o}$ is the longitudinal relaxation time of the liquid phase; and $T_{2,o}$ is the transverse relaxation time of the liquid;

providing a second matched filter having response which is matched to expected parameters of the gaseous phase; wherein the second matched filter $f(t)_g$ is given by the expression:

$$f(t)_g = HI_g[1-exp(-TR_2/T_{1,g})]exp(-t/T_{2,g}^\dagger) - HI_g[1-exp(-TR_1 T_{1,g})]exp(-t/T_{2,g}^\dagger(\tau_2/\tau_1)^2),$$

in which $HI_g$ is the hydrogen index of the gas phase; $T_{1,g}$ is the longitudinal relaxation time of the gaseous phase; and $T_{2,g}^\dagger$ is the apparent transverse relaxation time; and solving the matrix equation $A x=d(t)$ where $A=[f(t)_o f(t)_g]$; d(t) is the difference signal scaled in porosity units, and x is a solution vector, the first element of which is hydrogen liquid-filled porosity $\Phi_o$, and the second is gas-filled porosity $\Phi_g$.

17. The method of claim 16 further comprising the steps of:

reconstructing a liquid phase signal component on the basis of the solution vector x and the first matched filter $f(t)_o$;

reconstructing a gaseous phase signal component on the basis of the solution vector x and the second matched filter $f(t)_g$;

subtracting said liquid phase signal component and said gaseous phase signal component from a sum signal generated by pair-wise addition of the elements of the composite signal to obtain a water phase signal; and estimating water bound porosity $\Phi_W$ on the basis of the water phase signal.

18. The method of claim 1 wherein said first set of pulses is associated with a first measurement frequency; and said second set of pulses is associated with a second measurement frequency different from said first measurement frequency.

19. A system for determination of petrophysical properties of a geologic formation using NMR logging measurements comprising:

CPMG pulse generator providing a first set of CPMG pulses and at least one additional set of CPMG pulses, said first set being associated with a first recovery time $TR_1$ and said at least one additional set being associated with a recovery time $TR_i$ which is different from said first recovery time $TR_1$;

receiver of NMR echo signals responding to said first and said at least one additional set of CPMG pulses;

signal processor combining signals received in response to pulses in the first set and signals received in response to pulses in said at least one additional set to form a composite signal comprising data groups, each group corresponding to substantially the same depth mark in the formation;

wherein one element of each data group is associated with the first recovery time $TR_1$ and at least one different element of each data group is associated with recovery time $TR_i$ different from the first recovery time $TR_1$; and means for determining petrophysical properties of the geologic formation on the basis of the formed composite signal.

20. The system of claim 19 further comprising means for modifying the pulse echo spacing τ associated with CPMG pulses in the first set and said at least one additional set of CPMG pulses.

21. The system of claim 19 further comprising a first matched filter for identifying signal components associated with a hydrogen liquid phase of the formation; and a second matched filter for identifying signal components associated with the gaseous phase.

22. The system of claim 21 further comprising:

means for solving the matrix equation A x=d(t) where A=$[f(t)_o f(t)_g]$; d(t) is the difference signal scaled in porosity units, and x is a solution vector, the first element of which is hydrogen liquid-filled porosity $\Phi_o$, and the second is gas-filled porosity $\Phi_g$;

means for reconstructing a liquid phase signal component and a gaseous phase signal component on the basis of the solution vector x and the response of the first and the second matched filters; and means for estimating water bound porosity $\Phi_W$ on the basis of the reconstructed liquid phase signal component and the reconstructed gaseous phase signal component.

23. The system of claim 19 wherein each set of CPMG pulses is associated with a different measurement frequency.

24. A method for determination of petrophysical properties of a geologic formation using NMR logging measurements comprising the steps of:

providing two or more sets of CPMG pulses wherein each set is associated with recovery time $TR_i$;

receiving NMR echo signals in response to said two or more sets of CPMG pulses;

combining data representing NMR echo signals received in response to pulses in said two or more sets to form a composite signal comprising data groups, each group corresponding to substantially the same depth mark in the formation; wherein each of said recovery times $TR_i$ is associated with an element of each data group;

generating at least one difference signal by subtracting different elements of each data group; and determining petrophysical properties of the geologic formation on the basis of said at least one generated difference signal.

25. The method of claim 24 wherein each set of CPMG pulses is associated with a different measurement frequency.

26. A method for determination of petrophysical properties of a geologic formation using NMR logging measurements comprising the steps of:

providing a first set of CPMG pulses associated with a first recovery time $TR_1$;

providing a second set of CPMG pulses associated with a second recovery time $TR_2$;

receiving NMR echo signals in response to said first and said second set of CPMG pulses;

combining signals received in response to pulses in said first set and signals received in response to pulses in said second set to form a composite signal comprising data pairs, each pair corresponding to substantially the same depth mark in the formation; wherein one element of the data pair is associated with the first recovery time and a second element of the data pair is associated with the second recovery time;

processing said composite signal to minimize the contribution to said composite signal from a component in said geologic formation having a pre-specified longitudinal relaxation time; and determining petrophysical properties of the geologic formation on the basis of the processed composite signal.

27. The method of claim 26 wherein said first set of CPMG pulses is associated with a first measurement frequency and said second set of CPMG pulses is associated with a second measurement frequency different from said first measurement frequency.

28. A method for determination of petrophysical properties of a geologic formation using NMR logging measurements comprising the steps of:

providing a first set of CPMG pulses associated with a first recovery time $TR_1$;

providing a second set of CPMG pulses associated with a second recovery time $TR_2$;

wherein said first set of CPMG pulses is associated with a first measurement frequency and said second set of pulses is associated with a second measurement frequency different from said first measurement frequency;

receiving NMR echo signals in response to said first and said second set of CPMG pulses;

combining data representing NMR echo signals received in response to pulses in said first set and data representing NMR echo signals received in response to pulses in said second set to form a composite signal comprising data pairs, each pair corresponding to substantially the same depth mark in the formation;

wherein one element of the data pair is associated with the first recovery time and a second element of the data pair is associated with the second recovery time; and determining petrophysical properties of the geologic formation on the basis of the processed composite signal.

29. The method of claim 28 further comprising the step of:

processing said composite signal to minimize the contribution to said composite signal from a component in said geologic formation having a pre-specified longitudinal relaxation time.

\* \* \* \* \*